US008025889B2

(12) United States Patent
Walker

(10) Patent No.: US 8,025,889 B2
(45) Date of Patent: *Sep. 27, 2011

(54) BOTULINUM TOXIN ADMINISTRATION TO TREAT VARIOUS CONDITIONS

(75) Inventor: Patricia S. Walker, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 220 days.

This patent is subject to a terminal disclaimer.

(21) Appl. No.: 12/340,150

(22) Filed: Dec. 19, 2008

(65) Prior Publication Data
US 2010/0272754 A1 Oct. 28, 2010

Related U.S. Application Data

(63) Continuation of application No. 11/538,503, filed on Oct. 4, 2006, now Pat. No. 7,479,281, which is a continuation of application No. 10/051,952, filed on Jan. 17, 2002, now Pat. No. 7,255,865, which is a continuation-in-part of application No. 09/730,237, filed on Dec. 5, 2000, now abandoned.

(51) Int. Cl.
A61K 39/08 (2006.01)
C07K 14/33 (2006.01)

(52) U.S. Cl. .................. 424/239.1; 424/9.1; 424/236.1; 514/2; 514/12; 530/350; 530/412; 435/69.1; 435/69.7; 435/320.1; 435/325; 536/23.1

(58) Field of Classification Search .............. 424/239.1, 424/236.1, 9.1; 514/2, 12; 530/350, 412; 435/69.1, 69.7, 320.1, 325; 536/23.1
See application file for complete search history.

(56) References Cited

U.S. PATENT DOCUMENTS

| | | | |
|---|---|---|---|
| 5,183,462 | A | 2/1993 | Borodic |
| 5,437,291 | A | 8/1995 | Pasricha et al. |
| 5,721,215 | A | 2/1998 | Aoki et al. |
| 5,733,600 | A | 3/1998 | McCabe |
| 5,780,100 | A | 7/1998 | McCabe et al. |
| 5,922,685 | A | 7/1999 | Rakhmilevich et al. |
| D422,697 | S | 4/2000 | Bellhouse et al. |
| D428,650 | S | 7/2000 | Bellhouse et al. |
| 6,090,790 | A | 7/2000 | Eriksson |
| 6,306,423 | B1 | 10/2001 | Donovan et al. |
| 6,312,708 | B1 | 11/2001 | Donovan |
| 6,383,509 | B1 | 5/2002 | Donovan et al. |
| 6,464,986 | B1 | 10/2002 | Aoki et al. |
| 6,506,399 | B2 | 1/2003 | Donovan |
| 6,585,993 | B2 | 7/2003 | Donovan |
| 6,645,169 | B1 | 11/2003 | Slate et al. |
| 7,067,137 | B2 | 6/2006 | Aoki et al. |
| 7,255,865 | B2 | 8/2007 | Walker |
| 2002/0086036 | A1 | 7/2002 | Walker |
| 2004/0033241 | A1 | 2/2004 | Donovan et al. |
| 2004/0170665 | A1 | 9/2004 | Donovan |
| 2005/0214327 | A1 | 9/2005 | Brooks et al. |
| 2007/0020295 | A1 | 1/2007 | Donovan et al. |

FOREIGN PATENT DOCUMENTS

| | | |
|---|---|---|
| EP | 0 500 799 B1 | 1/1998 |
| WO | WO94/15629 | 7/1994 |
| WO | WO95/17904 | 7/1995 |
| WO | WO95/30431 | 11/1995 |

OTHER PUBLICATIONS

U.S. Appl. No. 11/538,503, filed Oct. 4, 2006, Walker, Patricia.
Manusov, Capt Eron G., et al., *Hyperhidrosis: A Management Dilemma*, The Journal of Family Practice, vol. 28, No. 4, 1998, pp. 412-415.
Bushara, K.O., et al., *Botulinum toxin—a possible treatment for axillary hyperhydrosis*, Clinical and Experimental Dermatology, 1996, pp. 276-278.
Odderson, Ib. R., *Hyperhidrosis Treated by Botulinum A Exotoxin*, Dermatol Surg, 1998, pp. 1237-1241.
Sato, K., *Hyperhidrosis*, JAMA, Feb. 6, 1991, 265(5), p. 651.
Ambache, N. *A further survey of the action of Clostridium botulinum toxin upon different types of autonomic nerve fibre*, The Journal of Physiology, 1951, vol. 113, No. 1, pp. 1-17.
American Academy of Pediatrics, Committee on Sports Medicine and Fitness, *Safety in Youth Ice Hockey: The Effects of Body Checking*, Pediatrics, vol. 105, No. 3, Mar. 2000.
Lauder, Tamara D., et al., *Sports and Physical Training Injury Hospitalizations in the Army*, Am J Prev Med, 2000, 18(35).
Lawton, Rob, et al., *Getting Back in the Game*, REHAB Management, Apr./May 1999, pp. 42-46.
Metzl, Jordan D., *Sports Medicine in Pediatric Practice: Keeping Pace with the Changing Times*, Pediatric Annals 29:3, Mar. 2000, pp. 146-148.
Habernek, Hans, et al., *Sport related proximal femoral fractures: a retrospective review of 31 cases treated in an eight year period*, Br. J. Sports Med, 2000, 24, pp. 54-58.
Cox, Carla, et al., *Prior Knee Injury and Risk of Future Hospitalization and Discharge from Military Service*, Am J. Prev Med 2000, 18(35), pp. 112-117.
Altcheck, David W., et al,. *The Painful Shoulder in the Throwing Athlete*, Orthopedic Clinics of North America, Apr. 2000, vol. 31, No. 2, pp. 241-245.
Varlotta, Gerard P., et al., *Professional Roller Hockey Injuries*, Clin J Sport Med, 2000, 10, pp. 29-33.
Nyland, John, et al,. *Soft Tissue Injuries to USA Paralympians at the 1996 Summer Games*, Arch Phys Med Rehabil, vol. 81, Mar. 2000, pp. 368-372.
Kenter, Keith, et al., *Acute Elbow Injuries in the National Football League*, J. Shoulder Elbow Surg, Jan./Feb. 2000, vol. 9, No. 1, pp. 1-5.
Sorli, Janet M., et al., *Equestrian injuries: a five year review of hospital admissions in British Columbia*, Canada, Injury Prevention, 2000, 6, pp. 59-61.
Howard, Paul D., *Differential Diagnosis of Calf Pain and Weakness: Flexor Hallucis Longus Strain*, Journal of Orthopaedic & Sports Physical Therapy, 2000, 30(2), pp. 78-84.

(Continued)

Primary Examiner — Chih-Min Kam
(74) Attorney, Agent, or Firm — Hal Gibson; Debra Condino

(57) ABSTRACT

Methods for treating conditions in an animal or human subject. The conditions may be pain, skeletal muscle conditions, smooth muscle conditions, glandular conditions and cosmetic conditions. The methods comprise the step of administering a *Clostridium* neurotoxin component or *Clostridium* neurotoxin component encoding DNA to the subject using a needleless syringe.

7 Claims, No Drawings

OTHER PUBLICATIONS

Cummins, Craig A., et al., *Current Concepts Review Suprascapular Nerve Entrapment*, The Journal of Bone and Joint Surgery, Inc., Mar. 2000, vol. 82-A, No. 3.

Watt, Fiona M., *Epidermal Stem Cells as Targets for Gene Transfer*, Human Gene Therapy, 11, Nov. 1, 2000, pp. 2261-2266.

Vogel, Jonathan C., *Nonviral Skin Gene Therapy*, Human Gene Therapy, Nov. 1, 2000, pp. 2253-2259.

Williams et al., *Introduction of foreign genes into tissues of living mice by DNA-coated microprojectiles*, Proc natl Acad Sci. USA, vol. 88, Apr. 1991, pp. 11478-11482.

Fynan, et al., *DNA vaccines: Protective immunizations by parenteral, mucosal, and gene-gun inoculations*, Proc Natl Acad Sci. USA, vol. 90, Dec. 1993, pp. 11478-11482.

Hengge, et al., *Expression of Naked DNA in Human, Pig, and Mouse Skin*, The Journal of Clinical Investigation, vol. 97, No. 12, Jun. 1996, pp. 2911-2916.

Waller, Anna E., et al., *Jockey Injuries in the United States*, JAMA, Mar. 8, 2000, vol. 283, No. 10.

Fehnel, David J., et al., *Anterior cruciate injuries in the skeletally immature athlete*, Sports Med Jan. 29, 2000, (1), pp. 51-63.

Kellmann, Michael et al., *Changes in stress and recovery in elite rowers during preparation for the Olympic Games*, Medicine & Science in Sports & Exercise, May 1999, pp. 676-683.

Major, Nancy M., et al,. *Sacral stress fractures in long-distance runners*, AJR, 174, Mar. 2000, pp. 727-729.

American Academy of Pediatrics, *Injuries in Youth Soccer: A subject review*, Committee on Sports Medicine and Fitness, Pediatrics, vol. 105, No. 3, Mar. 2000.

Jaivin, Jonathan S., *Foot Injuries and Artroscopy in Sport*, Sports Med Jan. 29, 2000 (1), pp. 65-72.

Canadian Medical Association, *No Pain, No Gain*?, Editorial, CMAJ, Jan. 25, 2000, 162(2).

Hulstyn, Michael J., et al,. *Diagnosis and Nonoperative Treatment of Common Athletic Shoulder Injuries*, Medicine and Health, Feb. 2, 2000, vol. 83, No. 2, pp. 40-44.

Brin, Mitchell F., *Interventional neurology: Treatment of neurological conditions with local injection of botulinum toxin*, Arch de Neruolbiol. 54, Supl. 3 (7-23) 1991.

Ambache, N., *The peripheral action of Clostridium botulinum toxin*, J Physiol, 1949, 108, pp. 127-141.

Dickson, Ernest C., et al., *Botulism, studies on the manner in which the toxin of Clostridium botulinum acts upon the body*, J Exper Med, 1923, v. 37.

*The Dermo-Jet*, A Robbins Exclusive. Web site of Robins Instruments, Inc. www.robinsinstruments.com/dermo-jet/dermojethome.html, Mar. 5, 2001.

Naumann, M., et al,. *Botulinum toxin for focal hyperhidrosis: Technical considerations and improvements in application*, Br. J. Dermatol, 1998, 139, pp. 1123-1124.

Vadoud-Sayedi, J., et al., *Treatment of Plantar Hyperhidrosis with dermojet injections of Botulinum Toxin*, Dermatology Sep. 2000, 201(2), p. 179.

Ishikawa, Hitoshi, et al., *Presynaptic Effects of Botulinum Toxin Type A on the Neuronally Eveoked Response of Albino and Pigmented Rabbit Iris Sphincter and Dilator Muscles*, Jpn J Ophthalmol, Mar. 4, 2000, 44(2), pp. 106-109.

Holder-Powell et al., *Unilateral Lower-Limb Musculoskeletal Injury: Its long-term effect on balance*, Arch Phys Med Rehabil, vol. 81, Mar. 2000.

Falo, Louis D., Jr., *Targeting the Skin for Genetic Immunizations*, Proceedings of the Association of American Physicians, vol. 111, No. 3, 1999, pp. 211-219.

Cao, et al., *Regulared Cutaneous Gene Delivery: The Skin as a Bioreactor*, Human Gene Therapy, Nov. 1, 2000, 11, pp. 2261-2266.

BOTULINUM TOXIN ADMINISTRATION TO TREAT VARIOUS CONDITIONS

RELATED APPLICATION

The present application is a continuation of application Ser. No. 11/538,503, filed Oct. 4, 2006, now U.S. Pat. No. 7,479,281, which is a continuation of application Ser. No. 10/051,952, filed Jan. 17, 2002, now U.S. Pat. No. 7,255,865, which is a continuation in part of application Ser. No. 09/730,237 filed Dec. 5, 2000, now abandoned, the disclosures of which are herein incorporated by reference in their entireties.

BACKGROUND OF THE INVENTION

Botulinum Toxin

The anaerobic, Gram positive bacterium *Clostridium botulinum* produces a potent polypeptide neurotoxin, *botulinum* toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The *botulinum* toxin can apparently pass unattenuated through the lining of the gut and attack peripheral motor neurons. Symptoms of *botulinum* toxin intoxication can progress from difficulty walking, swallowing, and speaking to paralysis of the respiratory muscles and death.

BoNT/A is the most lethal natural biological agent known to man. About 50 picograms of *botulinum* toxin (purified neurotoxin complex) serotype A is a $LD_{50}$ in mice. One unit (U) of *botulinum* toxin is defined as the amount of toxin that kills 50% of mice upon intraperitoneal injection into female Swiss Webster mice weighing 18-20 grams each. Seven immunologically distinct *botulinum* neurotoxins have been characterized, these being respectively *botulinum* neurotoxin serotypes A, B, $C_1$, D, E, F and G each of which is distinguished by neutralization with serotype-specific antibodies. The different serotypes of *botulinum* toxin vary in the animal species that they affect and in the severity and duration of the paralysis they evoke. For example, it has been determined that BoNt/A is 500 times more potent, as measured by the rate of paralysis produced in the rat, than is *botulinum* toxin serotype B (BoNT/B). Additionally, BoNt/B has been determined to be non-toxic in primates at a dose of 480 U/kg which is about 12 times the primate $LD_{50}$ for BoNt/A. *Botulinum* toxin apparently binds with high affinity to cholinergic motor neurons, is translocated into the neuron and blocks the release of acetylcholine.

*Botulinum* toxins have been used in clinical settings for the treatment of neuromuscular disorders characterized by hyperactive skeletal muscles. BoNt/A has been approved by the U.S. Food and Drug Administration for the treatment of blepharospasm, strabismus and hemifacial spasm. Non-serotype A *botulinum* toxin serotypes apparently have a lower potency and/or a shorter duration of activity as compared to BoNt/A. Clinical effects of peripheral intramuscular BoNt/A are usually seen within one week of injection. The typical duration of symptomatic relief from a single intramuscular injection of BoNt/A averages about three months.

Although all the *botulinum* toxins serotypes apparently inhibit release of the neurotransmitter acetylcholine at the neuromuscular junction, they do so by affecting different neurosecretory proteins and/or cleaving these proteins at different sites. For example, *botulinum* serotypes A and E both cleave the 25 kiloDalton (kD) synaptosomal associated protein (SNAP-25), but they target different amino acid sequences within this protein. BoNT/B, D, F and G act on vesicle-associated protein (VAMP, also called synaptobrevin), with each serotype cleaving the protein at a different site. Finally, *botulinum* toxin serotype $C_1$ (BoNT/$C_1$) has been shown to cleave both syntaxin and SNAP-25. These differences in mechanism of action may affect the relative potency and/or duration of action of the various *botulinum* toxin serotypes.

Regardless of serotype, the molecular mechanism of toxin intoxication appears to be similar and to involve at least three steps or stages. In the first step of the process, the toxin binds to the pre-synaptic membrane of the target neuron through a specific interaction between the H chain and a cell surface receptor; the receptor is thought to be different for each serotype of *botulinum* toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This last step is thought to be mediated by the amino end segment of the H chain, $H_N$, which triggers a conformational change of the toxin in response to a pH of about 5.5 or lower. Endosomes are known to possess a proton pump which decreases intra endosomal pH. The conformational shift exposes hydrophobic residues in the toxin, which permits the toxin to embed itself in the endosomal membrane. The toxin then translocates through the endosomal membrane into the cytosol.

The last step of the mechanism of *botulinum* toxin activity appears to involve reduction of the disulfide bond joining the H and L chain. The entire toxic activity of *botulinum* and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, *botulinum* toxin/B/D, /F, and /G cause degradation of synaptobrevin (also called vesicle-associated membrane protein (VAMP)), a synaptosomal membrane protein. Most of the VAMP present at the cytosolic surface of the synaptic vesicle is removed as a result of any one of these cleavage events. Each toxin specifically cleaves a different bond.

The molecular weight of the *botulinum* toxin protein molecule, for all seven of the known *botulinum* toxin serotypes, is about 150 kD. Interestingly, the *botulinum* toxins are released by Clostridial bacterium as complexes comprising the 150 kD *botulinum* toxin protein molecule along with associated non-toxin proteins. Thus, the BoNt/A complex can be produced by Clostridial bacterium as 900 kD, 500 kD and 300 kD forms. BoNT/B and $C_1$ are apparently produced as only a 500 kD complex. BoNT/D is produced as both 300 kD and 500 kD complexes. Finally, BoNT/E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the *botulinum* toxin molecule comprise the relevant neurotoxin complex) may act to provide stability against denaturation to the *botulinum* toxin molecule and protection against digestive acids when toxin is ingested. Additionally, it is possible that the larger (greater than about 150 kD molecular weight) *botulinum* toxin complexes may result in a slower rate of diffusion of the *botulinum* toxin away from a site of intramuscular injection of a *botulinum* toxin complex.

In vitro studies have indicated that *botulinum* toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine, CGRP and glutamate.

BoNt/A can be obtained by establishing and growing cultures of *Clostridium botulinum* in a fermenter and then harvesting and purifying the fermented mixture in accordance with known procedures. All the *botulinum* toxin serotypes are initially synthesized as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the BoNt/B serotype only cleave a portion of the toxin produced. The exact proportion of nicked to unnicked molecules depends on the length of incubation and the temperature of the culture. Therefore, a certain percentage of any preparation of, for example, the BoNt/B toxin is likely to be inactive, possibly accounting for the known significantly lower potency of BoNt/B as compared to BoNt/A. The presence of inactive *botulinum* toxin molecules in a clinical preparation will contribute to the overall protein load of the preparation, which has been linked to increased antigenicity, without contributing to its clinical efficacy. Additionally, it is known that BoNt/B has, upon intramuscular injection, a shorter duration of activity and is also less potent than BoNt/A at the same dose level.

It has been reported that BoNt/A has been used in clinical settings as follows:

(1) about 75-125 units of BOTOX®[1] per intramuscular injection (multiple muscles) to treat cervical dystonia;

[1] Available from Allergan, Inc., of Irvine, Calif. under the tradename BOTOX®.

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the subject receives from 90 U to 360 U of upper limb flexor muscle BOTOX® by intramuscular injection at each treatment session.

The success of BoNt/A to treat a variety of clinical conditions has led to interest in other *botulinum* toxin serotypes. A study of two commercially available BoNT/A preparations (BOTOX® and Dysport®) and preparations of BoNT/B and F (both obtained from Wako Chemicals, Japan) has been carried out to determine local muscle weakening efficacy, safety and antigenic potential. *Botulinum* toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves. Additional mice were given intramuscular injections to determine $LD_{50}$ doses. The therapeutic index was calculated as $LD_{50}/ED_{50}$. Separate groups of mice received hind limb injections of BOTOX® (5.0 to 10.0 units/kg) or BoNt/B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for BoNt/B or 0.15 ng/kg for BOTOX®). Peak muscle weakness and duration were dose related for all serotypes. DAS $ED_{50}$ values (units/kg) were as follows: BOTOX®: 6.7, Dysport®: 24.7, BoNt/B: 27.0 to 244.0, BoNT/F: 4.3. BOTOX® had a longer duration of action than BoNt/B or BoNt/F. Therapeutic index values were as follows: BOTOX®: 10.5, Dysport®: 6.3, BoNt/B: 3.2. Water consumption was greater in mice injected with BoNt/B than with BOTOX®, although BoNt/B was less effective at weakening muscles. After four months of injections 2 of 4 (where treated with 1.5 ng/kg) and 4 of 4 (where treated with 6.5 ng/kg) rabbits developed antibodies against BoNt/B. In a separate study, 0 of 9 BOTOX® treated rabbits demonstrated antibodies against BoNt/A. DAS results indicate relative peak potencies of BoNt/A being equal to BoNt/F, and BoNt/F being greater than BoNt/B. With regard to duration of effect, BoNt/A was greater than BoNt/B, and BoNt/B duration of effect was greater than BoNt/F. As shown by the therapeutic index values, the two commercial preparations of BoNt/A (BOTOX® and Dysport®) are different. The increased water consumption behavior observed following hind limb injection of BoNt/B indicates that clinically significant amounts of this serotype entered the murine systemic circulation. The results also indicate that in order to achieve efficacy comparable to BoNt/A, it is necessary to increase doses of the other serotypes examined. Increased dosage can comprise safety. Furthermore, in rabbits, serotype B was more antigenic than was BOTOX®, possibly because of the higher protein load injected to achieve an effective dose of BoNt/B.

The tetanus neurotoxin acts mainly in the central nervous system, while *botulinum* neurotoxin acts at the neuromuscular junction; both act by inhibiting acetylcholine release from the axon of the affected neuron into the synapse, resulting in paralysis. The effect of intoxication on the affected neuron is long-lasting and until recently has been thought to be irreversible. The tetanus neurotoxin is known to exist in one immunologically distinct serotype.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic and most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of the heart by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic neurons of the parasympathetic nervous system, as well as in those stimulated by the postganglionic cholinergic neurons of the sympathetic nervous system. The nicotinic receptors are found in the synapses between the preganglionic and postganglionic neurons of both the sympathetic and parasympathetic. The nicotinic receptors are also present in many membranes of skeletal muscle fibers at the neuromuscular junction.

Acetylcholine is released from cholinergic neurons when small, clear, intracellular vesicles fuse with the pre-synaptic neuronal cell membrane. A wide variety of non-neuronal secretory cells, such as, adrenal medulla (as well as the PC12 cell line) and pancreatic islet cells release catecholamines and insulin, respectively, from large dense-core vesicles. The PC12 cell line is a clone of rat pheochromocytoma cells extensively used as a tissue culture model for studies of sympathoadrenal development. *Botulinum* toxin inhibits the release of both types of compounds from both types of cells in vitro, permeabilized (as by electroporation) or by direct injection of the toxin into the denervated cell. *Botulinum* toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

*Botulinum* toxin has been shown to be effective in treating a number of conditions. For example, *botulinum* toxin may alleviate hyperhidrosis for up to 11 months. Odderson, *Dermatol Surg* (1988) 24:1237-1241, discloses that intracutaneous injections of *botulinum* toxin type A to the sweating area of the skin reduces excessive sweating; and Bushara et al., *Clinical and Experimental Dermatology* (1996) 21:276-278, disclose that subcutaneous injections of *botulinum* toxin type A can selectively denervate the local sweat glands to produce an anhidrotic patch.

Skin gene therapy is an effective method to directly deliver and transiently express genes in the skin. Several different delivery methods have been successfully used in recent years. Three of these delivery methods are needleless injection, topical gene delivery and direct gene delivery by injection using a needle.

In needleless injection delivery methods, microprojectile carrier particles may be coated with DNA encoding the desired gene and then discharged into the skin from an external delivery device. Depending on the discharge velocity and the distance from the injection site, the drug particles penetrate through the stratum corneum to different layers of the epidermis, dermis and underlying muscle. As the DNA-coated microprojectiles penetrate through epidermal and dermal cells, or are deposited in these cells, DNA is released and the encoded genes can be expressed. The cells potentially targeted by these drug particles in the epidermis include, but are not limited to keratinocytes, melanocytes and Langerhans cells. In the dermis fibroblasts, endothelial cells, adipocytes and dermal dendritic cells may be potential targets. If the microprojectiles penetrate through the dermis, underlying muscle cells could be targeted. One important aspect of this mechanism of delivery is that the DNA is directly delivered into the cell by penetration. Therefore, the issue of skin cell's ability to uptake DNA is not relevant. This means that all skin cells exposed to the DNA coated microprojectiles are potential targets.

In topical gene delivery, DNA can be applied to the skin as either a liposomal-DNA mixture or as an uncoated DNA for epicutaneous transfer into the epidermis. Primarily epidermal cells would be targeted with this delivery method. However, other cells may be targeted with needles Gene delivery by injection with a needle is another method of gene delivery to the skin. With this method, the DNA is typically introduced directly into the dermis. Both epidermal and dermal cells have access to and can express the DNA. Electroinjection and electroporation methods of delivery are modifications of the direct injection method where a needle is used. These two methods can result in a higher level of gene expression than conventional injection using a needle. After intradermal injection of the DNA, electric pulses are applied to the injected area by electrodes for improved cellular uptake.

All these methods of gene delivery can be used for expression of *botulinum* toxin encoding DNA.

SUMMARY OF THE INVENTION

The present invention provides new and improved methods for the injection of *botulinum* toxin into an animal or human subject. The present invention also provides for methods for injecting *botulinum* toxin encoding DNA into an animal or human subject.

In accordance with the present invention, there are provided methods for treating a condition in an animal or human subject. These conditions may comprise pain, skeletal muscle conditions, smooth muscle conditions and glandular conditions. *Botulinum* toxins are also used for cosmetic purposes. The methods may comprise a step of administering a *Clostridium* neurotoxin component to the subject using a needleless syringe.

In one embodiment, the neurotoxin component is administered with a carrier, wherein the neurotoxin is coated on the carrier. In another embodiment, the neurotoxin is mixed with the carrier. The carrier may comprise a dense material, for example, gold, platinum, tungsten or ice.

Still further in accordance with the present invention, the condition treated may be spasmodic dysphonia, laryngeal dystonia, oromandibular dysphonia, lingual dystonia, cervical dystonia, focal hand dystonia, blepharospasm, strabismus, hemifacial spasm, eyelid disorder, cerebral palsy, focal spasticity, spasmodic colitis, neurogenic bladder, anismus, limb spasticity, tics, tremors, bruxism, anal fissure, achalasia, fibromyalgia, dysphagia, lacrimation, hyperhydrosis, excessive salivation, excessive gastrointestinal secretions, excessive mucous secretion, pain from muscle spasms, headache pain, brow furrows and skin wrinkles.

Still further in accordance with the present invention, the neurotoxin component may be administered to the skin. The skin may comprise an epidermis layer, a dermis layer and a hypodermis layer.

In one embodiment, the neurotoxin component is administered to one or more layers of a skin where a nerve is located.

In another embodiment, the neurotoxin component is administered to a skin and substantially to a muscle tissue.

In still another embodiment, the neurotoxin component is administered to a muscle tissue.

Still further in accordance with the present invention, the neurotoxin component may be a *difficile* toxin, a *butyricum* toxin a *tetani* toxin or a *botulinum* toxin type A, B, $C_1$, D, E, F, or G or a variant thereof.

Still further in accordance with the present invention, the neurotoxin component may comprise a targeting component, a therapeutic component and a translocation component.

In one embodiment, the targeting component binds to a cell, for example, a nerve cell. In one embodiment the targeting component binds to a pre-synaptic nerve terminal. The pre-synaptic nerve terminal may belong to a cholinergic neuron.

The targeting component may comprise, for example, a carboxyl end segment of a heavy chain of a *butyricum* toxin, a *tetani* toxin or a *botulinum* toxin type A, B, $C_1$, D, E, F, G or a variant thereof.

In one embodiment, the therapeutic component substantially interferes with exocytosis from a cell, for example, interfering with the release of neurotransmitters from a neuron or its terminals.

The therapeutic component may comprise, for example, a light chain of a *butyricum* toxin, a *tetani* toxin or a *botulinum* toxin type A, B, $C_1$, D, E, F, G or a variant thereof.

In one embodiment, the translocation component facilitates transfer of at least a part of the neurotoxin component into the cytoplasm of a target cell.

The translocation component may comprise, for example, an amino end fragment of a heavy chain of a *butyricum* toxin, a *tetanti* toxin or a *botulinum* toxin type A, B, $C_1$, D, E, F, G or a variant thereof.

The targeting component may comprise, for example, a carboxyl end fragment of a heavy chain of a *botulinum* toxin type A, the therapeutic component may comprise a light chain of a *botulinum* toxin type A and the translocation component may comprise an amine end fragment of a heavy chain of *botulinum* toxin type A.

Still further in accordance with the present invention, the neurotoxin component may be recombinantly produced.

Still further in accordance with the present invention, are methods for expressing a recombinant DNA sequence encoding a *Clostridium* neurotoxin component in a cell of an animal in situ. The cell may be, for example, a skin cell, a muscle cell or a nerve cell.

In one embodiment, the DNA is administered to the animal by injection. For example, the injection may be by needleless injection.

Still further in accordance with the present invention, the DNA encoding neurotoxin component may be a *difficile* toxin, a *butyricum* toxin, a *tetani* toxin or a *botulinum* toxin type A, B, $C_1$, D, E, F, or G or a variant thereof.

In one embodiment, the DNA encoding neurotoxin component comprises a targeting component, a therapeutic component and a translocation component.

Still further in accordance with the present invention, the targeting component may bind to a cell, for example, a nerve cell. In one embodiment, the targeting component binds to a pre-synaptic nerve terminal. The pre-synaptic nerve terminal may belong to a cholinergic neuron.

Still further in accordance with the present invention, the targeting component may comprise a carboxyl end segment of a heavy chain of a *butyricum* toxin, a *tetani* toxin or a *botulinum* toxin type A, B, $C_1$, D, E, F, G or a variant thereof.

Still further in accordance with the present invention, the therapeutic component may substantially interfere with exocytosis from a cell, for example, interfering with the release of neurotransmitters from a neuron or its terminals.

The therapeutic component may comprise, for example, a light chain of a *butyricum* toxin, a *tetani* toxin or a *botulinum* toxin type A, B, $C_1$, D, E, F, G or a variant thereof.

Still further in accordance with the present invention, the translocation component may facilitate transfer of at least a part of the neurotoxin component into the cytoplasm of a target cell.

The translocation component may comprise, for example, an amino end fragment of a heavy chain of a *butyricum* toxin, a tetnus toxin or a *botulinum* toxin type A, B, $C_1$, D, E, F, G or a variant thereof.

In one embodiment, the targeting component comprises a carboxyl end fragment of a heavy chain of a *botulinum* toxin type A, the therapeutic component comprises a light chain of a *botulinum* toxin type A, and the translocation component comprises an amine end fragment of a heavy chain of *botulinum* toxin type A.

Still further in accordance with the present invention, the neurotoxin component may be recombinantly produced.

Still further in accordance with the present invention, are compositions that may comprise a carrier and a Clostridial neurotoxin component, the composition may be useful for delivery of said neurotoxin component to a cell of an animal in situ.

The carrier may be a dense material for example gold, tungsten, platinum or ice crystal.

Still further in accordance with the present invention, the neurotoxin component may be a *difficile* toxin, a *butyricum* toxin a *tetani* toxin or a *botulinum* toxin type A, B, $C_1$, D, E, F, or G or a variant thereof.

Still further in accordance with the present invention, the neurotoxin component comprises a targeting component, a therapeutic component and a translocation component.

Still further in accordance with the present invention, the targeting component may bind to a cell, for example, a nerve cell. In one embodiment, the targeting component binds to pre-synaptic nerve terminal. The pre-synaptic nerve terminal may belong to a cholinergic neuron.

Still further in accordance with the present invention, the targeting component may comprise a carboxyl end segment of a heavy chain of a *butyricum* toxin, a *tetani* toxin or a *botulinum* toxin type A, B, $C_1$, D, E, F, G or a variant thereof.

In one embodiment, the therapeutic component substantially interferes with exocytosis from a cell, for example, interfering with the release of neurotransmitters from a neuron or its terminals.

The therapeutic component may comprise, for example, a light chain of a *butyricum* toxin, a *tetani* toxin or a *botulinum* toxin type A, B, $C_1$, D, E, F, G or a variant thereof.

Still further in accordance with the present invention, the translocation component may facilitate transfer of at least a part of the neurotoxin component into the cytoplasm of a target cell.

The translocation component may comprise, for example, an amino end fragment of a heavy chain of a *butyricum* toxin, a *tetanti* toxin or a *botulinum* toxin type A, B, $C_1$, D, E, F, G or a variant thereof.

In one embodiment, the targeting component comprises a carboxyl end fragment of a heavy chain of a *botulinum* toxin type A, the therapeutic component comprises a light chain of a *botulinum* toxin type A, and the translocation component comprises an amine end fragment of a heavy chain of *botulinum* toxin type A.

Still further in accordance with the present invention, is a method to treat a condition in a subject comprising administering a therapeutically effective amount of DNA encoding a Clostridial neurotoxin component to a cell of an animal, for example, a human subject in situ. The cell may be, for example, a skin cell, a muscle cell or a nerve cell.

In one embodiment, the DNA is administered to the subject by injection. For example, the injection may be by needleless injection.

Still further in accordance with the present invention, the condition may comprise pain, skeletal muscle conditions, smooth muscle conditions and/or glandular conditions. In addition, DNA encoding a Clostridial neurotoxin may be administered to a subject for cosmetic purposes. For example, the condition may be spasmodic dysphonia, laryngeal dystonia, oromandibular dysphonia, lingual dystonia, cervical dystonia, focal hand dystonia, blepharospasm, strabismus, hemifacial spasm, eyelid disorder, cerebral palsy, focal spasticity, spasmodic colitis, neurogenic bladder, anismus, limb spasticity, tics, tremors, bruxism, anal fissure, achalasia, fibromyalgia, dysphagia, lacrimation, hyperhydrosis, excessive salivation, excessive gastrointestinal secretions, excessive mucous secretion, pain from muscle spasms, headache pain, brow furrows and skin wrinkles.

Still further in accordance with the present invention, are methods for immunization which include administering an effective amount of DNA encoding a Clostridial neurotoxin component to a tissue, for example, the skin, of a subject. The administering may be by injection, for example, by needleless injection.

Still further in accordance with the present invention, are compositions comprising a carrier and a DNA sequence encoding a Clostridial neurotoxin which may be useful for delivery of the DNA to a cell of a an animal or human subject in situ.

Still further in accordance with the present invention, the DNA encoding a neurotoxin may encode, for example, *botulinum* type A, B, $C_1$, D, E, F, G or mixtures thereof or combinations thereof.

Any and all features described herein and combinations of such features are included within the scope of the invention provided that such features of any such combination are not mutually exclusive.

These and other aspects and advantages of the present invention are apparent in the following detailed description and claims.

DEFINITIONS

Before proceeding to describe the present invention, the following definitions are provided and apply herein.

"Affected skin area" means an area which may be in the vicinity of the area to be treated by needleless injection, for example, an area of skin at or near an area of skin with excessive sweating.

"Drug particle" means a drug, for example, a neurotoxin or, for example, a DNA sequence encoding a neurotoxin, alone, or in combination with one or more other substances, for example, gold.

"Without using a needle" or "needleless injection" means injecting a measurable amount of substance, for example, a carrier coated with a *botulinum* toxin without the use of a standard needle.

"Heavy chain" means the heavy chain of a Clostridial neurotoxin. It preferably has a molecular weight of about 100 kDa and may be referred to herein as H chain or as H.

"$H_N$" means a fragment (preferably having a molecular weight of about 50 kDa) derived from the H chain of a Clostridial neurotoxin which is approximately equivalent to the amino terminal segment of the H chain, or the portion corresponding to that fragment in the intact in the H chain. It is believed to contain the portion of the natural or wild type Clostridial neurotoxin involved in the translocation of the L chain across an intracellular endosomal membrane.

"$H_C$" means a fragment (about 50 kDa) derived from the H chain of a Clostridial neurotoxin which is approximately equivalent to the carboxyl terminal segment of the H chain, or the portion corresponding to that fragment in the intact H chain. It is believed to be immunogenic and to contain the portion of the natural or wild type Clostridial neurotoxin involved in high affinity, pre-synaptic binding to motor neurons.

"Light chain" means the light chain of a Clostridial neurotoxin. It preferably has a molecular weight of about 50 kDa, and can be referred to as L chain, L or as the proteolytic domain (amino acid sequence) of a Clostridial neurotoxin. The light chain is believed to be effective as an inhibitor of neurotransmitter release when it is released into a cytoplasm of a target cell.

"Neurotoxin" means a chemical entity that is capable of interfering with the functions of a neuron. For example, a neurotoxin may interfere with the transmission of an electrical signal from a nerve cell to its target. The target may be, for example, another nerve cell, a tissue or an organ. The "neurotoxin" may be naturally occurring or other.

"Variant" means a chemical entity which is slightly different from a parent chemical entity but which still has a biological effect similar, or substantially similar to the biological effect of the chemical entity. The biological effect of the variant may be substantially the same or better than that of the parent. For example, a variant neurotoxin component may have one or more amino acid substitutions, amino acid modifications, amino acid deletions and/or amino acid additions. An amino acid substitution may be conservative or non-conservative, as is well understood in the art. In addition, variants of neurotoxin components may include neurotoxin components that have modified amino acid side chains, as is well known in the art. Variants may also include fragments.

An example of a variant neurotoxin component may comprise a variant light chain of a *botulinum* toxin having one or more amino acids substituted, modified, deleted and/or added. This variant light chain may have the same or better ability to prevent exocytosis, for example, the release of neurotransmitter vesicles. Additionally, the biological effect of a variant may be decreased compared to the parent chemical entity. For example, a variant light chain of a *botulinum* toxin type A having an amino acid sequence removed may have a shorter biological persistence than that of the parent (or native) *botulinum* toxin type A light chain.

"Fragment" means an amino acid or nucleotide sequence that comprises 1% or more of the parent amino acid or nucleotide sequence. For example, a fragment of *botulinum* toxin type A comprises 1% or more of the amino acid sequence of *botulinum* type A.

DETAILED DESCRIPTION OF THE INVENTION

Methods for administering neurotoxins, and DNA encoding neurotoxins, to animals, for example, humans are disclosed herein. In one broad embodiment, methods for administering neurotoxins include a step of administering a neurotoxin without using a needle. In another broad embodiment, there are provided methods of administering a DNA nucleotide sequence which encodes a neurotoxin to an animal or human subject.

Using these methods of administration, *botulinum* toxin can be used to treat a variety of conditions that are benefited by *botulinum* toxin treatment. For example, spasmodic dysphonia, laryngeal dystonia, oromandibular dysphonia, lingual dystonia, cervical dystonia, focal hand dystonia, blepharospasm, strabismus, hemifacial spasm, eyelid disorder, cerebral palsy, focal spasticity, spasmodic colitis, neurogenic bladder, anismus, limb spasticity, tics, tremors, bruxism, anal fissure, achalasia, fibromyalgia, dysphagia, lacrimation, hyperhydrosis, excessive salivation, excessive gastrointestinal secretions, as well as other secretory disorders, pain from muscle spasms, headache pain, brow furrows and skin wrinkles and other muscle tone disorders, and other disorders, characterized by involuntary movements of muscle groups may be treated using the present methods of administration. Further, the methods of administration of the present invention are useful for immunization against a neurotoxin.

The skin has two distinct layers and varies in thickness from about 1.5 to about 4 mm or more, depending on the regions of the body. The first layer is the superficial layer called the epidermis. It is a relatively thick epithelium. Deep to the epidermis is the second layer called the dermis. The dermis is a fibrous connective tissue and comprises sweat glands and nerves, or nerve terminals, innervating such sweat glands.

Just below the skin lies a fatty layer called the hypodermis, which may also be considered a part of a subcutaneous layer. Beneath the hypodermis or subcutaneous layer lies the deep fascial investment of the specialized structures of the body, for example the muscles.

Accordingly, the method of this invention delivers a neurotoxin, or DNA encoding a neurotoxin, to a tissue of an animal or a human subject. In one embodiment, the drug is delivered to the layer of the skin in which nerve terminals are found. For example, delivery is to the dermis layer. In another embodiment, delivery is to at least one layer of the skin and substantially to tissues beneath. For example, the administration to the dermis layer of the skin and to the subcutaneous layer. In another embodiment, delivery is to the skin and to muscle tissues beneath. In still another embodiment, delivery is substantially to the muscle tissue.

The administration of a composition comprising a carrier and a neurotoxin component and/or DNA encoding a neurotoxin component according to the invention may be accomplished through the use of a needleless injector. Needleless injectors and their use are well known in the art. For example, Bellhouse et al. in U.S. Pat. Nos. 6,053,889 ('889), 6,013,050 ('050), 6,010,478 ('478), 6,004,286 ('286) and 5,899,880 ('880) disclose novel needleless injectors. The disclosures therein are incorporated in their entirety by reference herein. In one embodiment, the needleless injector comprises an elongated tubular nozzle and is connected to or capable of connection to a suitable energizing means for producing a supersonic gas flow, for example a burst of helium, which accelerates mediums to high velocity toward a skin surface and into the skin surface. Such a device may be purchased from PowderJect Pharmaceuticals, Oxford, UK. In one embodiment, the gas pressure provided must be sufficient to discharge the compositions into a targeted site, for example the dermis, but not so great as to damage the target. In another embodiment, the gas pressure provided is sufficient to deliver the compositions to a target site, for example the dermis, but not so great as to damage the skin surface, for example the epithelium. In another embodiment, the gas pressure is sufficient to deliver the compositions to the dermis layer, but not to the layers below, for example the subcutaneous layer and/or the muscle tissues. In another embodiment, the gas pressure provided must be sufficient to discharge the drug particles into a targeted site, for example the dermis and/or substantially to the muscle tissue below, but not so great as to damage the skin surface.

Advantages for using a needleless injector according to the present invention include, for example, an optimal delivery to a specific tissue layer, for example the dermis layer. Furthermore, in the case where the delivery is to the dermis and not the muscle tissues, the treatment may not cause a loss of motor function in the area being treated. Also, the use of a needleless injector according to the present invention improves clinical safety by eliminating the risk of infection from accidental injury with needles or from potential splash back of bodily fluids from liquid jet injectors, thereby avoiding the possibilities of cross-contamination of blood-borne pathogens such as HIV and hepatitis B. The needleless injector, such as the PowderJect System, also offers an optimal and specific delivery of drug particles to treat conditions with little pain or skin damage such as bruising or bleeding.

A drug particle may comprise a neurotoxin component and a carrier component. The neurotoxin may include a targeting component, a therapeutic component and a translocation component. The targeting component may bind to a pre-synaptic nerve terminal, for example a pre-synaptic nerve terminal of a cholinergic neuron. For example, the targeting component may include a carboxyl end segment of a heavy chain of a *butyricum* toxin, a *tetani* toxin, a *botulinum* toxin type A, B, $C_1$, D, E, F, G, or a variant thereof. In a preferred embodiment, the targeting component comprises a carboxyl end segment of a heavy chain of a *botulinum* toxin type A.

The therapeutic component may substantially interfere with exocytosis from a cell, for example, interfering with the release of neurotransmitters from a neuron or its terminals. For example, the therapeutic component may include a light chain of a *butyricum* toxin, a *tetani* toxin, a *botulinum* toxin type A, B, $C_1$, D, E, F, G, or a variant thereof. In a preferred embodiment, the therapeutic component comprises a light chain of a *botulinum* toxin type A.

The translocation component may facilitate the transfer of at least a part of the neurotoxin into the cytoplasm of the target cell. For example, the translocation component may include an amino end fragment of a heavy chain of a *butyricum* toxin, a *tetani* toxin, a *botulinum* toxin type A, B, $C_1$, D, E, F, G or a variant thereof. In a preferred embodiment, the translocation component comprises an amino end fragment of a heavy chain of a *botulinum* toxin type A.

In one embodiment, the targeting component comprises a carboxyl end fragment of a heavy chain of a *botulinum* toxin type A, the therapeutic component comprises a light chain of a *botulinum* toxin type A and the translocation component comprises an amine end fragment of a heavy chain of a *botulinum* toxin type A. In a preferred embodiment, the neurotoxin of the present invention comprises a *botulinum* toxin type A. For example, very useful *botulinum* toxin type A may be obtained from Allergan, Inc., under the trade name BOTOX®.

In another broad aspect of this invention, recombinant techniques are used to produce at least one of the components of the neurotoxins. The technique includes steps of obtaining DNA sequences which encode at least one of the neurotoxin components, for example the therapeutic component, translocation component and/or targeting component. The DNA encoding the neurotoxin is inserted into an expression vector with compatible cohesive end terminals that will allow for the annealing and subsequent ligation of the neurotoxin encoding DNA insert. After ligation the recombinant DNA molecules are transformed into a host cell such as *E. coli*. Transformants are screened for by, for example, blue-white screening, as is known in the art. After identification of a recombinant vector containing the appropriate insert by for example, restriction digest analysis and/or nucleotide sequence analysis, the recombinant neurotoxin is expressed using either a constitutive or inducible promoter depending on the type of expression vector used. The recombinant protein produced by the expression system can be isolated using conventional techniques. For example, if an expression vector which produces a polyhis-factor Xa fusion protein is used, the protein can be first isolated on a metal containing column, such as a nickel, and then cleaved with factor Xa to release the neurotoxin molecule. Many variations for producing neurotoxins by recombinant methodologies exist and are familiar to those skilled in the art. For example, yeast, mammalian or insect cell systems may be used to produce recombinant neurotoxin proteins.

The recombinant protein may comprise all three components of the neurotoxin. For example, the protein expressed may include a light chain of *botulinum* toxin type E (the therapeutic component), a heavy chain, preferably the $H_N$, of a *botulinum* toxin type B (the translocation component), and an $H_C$ of *botulinum* toxin type A, which selectively binds to the motor neurons. In one embodiment, the protein expressed may include less than all three components of the neurotoxin. In such case, the components may be chemically joined using techniques known in the art.

There are many advantages to producing these neurotoxins recombinantly. For example, production of neurotoxin from anaerobic *Clostridium* cultures is a cumbersome and time-consuming process including a multi-step purification protocol involving several protein precipitation steps and either prolonged and repeated crystallization of the toxin or several stages of column chromatography. Significantly, the high toxicity of the product dictates that the procedure must be performed under strict containment (BL-3). During the fermentation process, the folded single-chain neurotoxins are activated by endogenous Clostridial proteases through a process termed nicking. This involves the removal of approximately 10 amino acid residues from the single-chain to create the di-chain form in which the two chains remain covalently linked through the intrachain disulfide bond.

The nicked neurotoxin is much more active than the unnicked form. The amount and precise location of nicking varies with the serotypes of the bacteria producing the toxin. The differences in single-chain neurotoxin activation and, hence, the yield of nicked toxin, are due to variations in the type and amounts of proteolytic activity produced by a given strain. For example, greater than 99% of *Clostridial botulinum* type A single-chain neurotoxin is activated by the Hall A *Clostridial botulinum* strain, whereas type B and E strains produce toxins with lower amounts of activation (0 to 75% depending upon the fermentation time). Thus, the high toxicity of the mature neurotoxin plays a major part in the commercial manufacture of neurotoxins as therapeutic neurotoxins.

The degree of activation of engineered Clostridial toxins is, therefore, an important consideration for manufacture of these materials. It would be a major advantage if neurotoxins such as *botulinum* toxin and tetanus toxin could be expressed, recombinantly, in high yield in rapidly-growing bacteria (such as heterologous *E. coli* cells) as relatively non-toxic single-chains (or single chains having reduced toxic activity) which are safe, easy to isolate and simple to convert to the fully-active form.

With safety being a prime concern, previous work has concentrated on the expression in *E. coli* and purification of individual H and L chains of tetanus and *botulinum* toxins; these isolated chains are, by themselves, non-toxic; see Li et al., *Biochemistry* 33:7014-7020 (1994); Zhou et al., *Biochemistry* 34:15175-15181 (1995), hereby incorporated by reference herein. Following the separate production of these peptide chains and under strictly controlled conditions the H and L subunits can be combined by oxidative disulphide linkage to form the neuroparalytic di-chains.

In another embodiment, a DNA nucleotide sequence encoding a neurotoxin is injected into an animal or human subject. For example, the DNA nucleotide sequence may be that of *botulinum* toxin type A (SEQ. ID. #1), type B (SEQ. ID. #2 and #3), type $C_1$ (SEQ. ID #4), type D (SEQ. ID. #5), type E (SEQ. ID. #6 and #7), type F (SEQ. ID. #8) and type G (SEQ. ID. #9), variants thereof or fragments thereof. In one embodiment, the injected DNA nucleotide sequence encodes a Clostridial toxin or a variant of a Clostridial toxin. In one embodiment the nucleotide sequence encodes a *botulinum* toxin type A. In another embodiment the DNA nucleotide sequence encodes a fragment of a neurotoxin. For example, the DNA sequence may encode a therapeutic component, for example, a light chain of a *botulinum* toxin.

Injection of the DNA nucleotide sequence may be, for example, to treat a condition in an animal, for example a human. Injection of a DNA nucleotide sequence encoding a Clostridial toxin may also be used to immunize an animal or human subject.

Injection of the DNA nucleotide sequence may also be used for research purposes. For example, these methods may be used to examine the expression of Clostridial genes inside an animal cell in situ. Also, for example, activity of a neurotoxin inside of an animal cell in situ may be studied using these methods.

A neurotoxin or DNA sequence encoding a neurotoxin may be injected alone, or in combination with other drugs and/or agents. In either case, the neurotoxin or DNA sequence encoding a neurotoxin may be prepared as pharmaceutical compositions. The composition may contain one or more added materials such as carriers and/or excipients. As used herein, "carriers" and "excipients" generally refer to substantially inert, non-toxic materials that do not deleteriously interact with other components of the composition. These materials may be used to increase the amount of solids in particulate pharmaceutical compositions, such as to form a powder of drug particles suitable for use with a needleless injector. Examples of suitable carriers include water, silicone, gelatin, waxes, and the like. Although a naked DNA nucleotide sequence may be injected in accordance with this invention, it is preferable that the injected DNA be accompanied by a carrier, for example See Felgner et al, U.S. Pat. No. 5,459,127, the disclosure of which is incorporated in its entirety herein by reference.

Other suitable carriers include any high density, biologically inert materials. For example, tungsten, platinum, iridium gold and/or ice crystal may be employed as carriers. In one embodiment, the carrier is less than about 10 mm, more preferably less than about 5 mm, even more preferably less than about 3 mm. High density carriers of such size may readily enter living cells without unduly injuring such cells. In one embodiment, a drug particle comprises a neurotoxin, for example *botulinum* toxin type A, and a carrier, for example a high density material of less than 5 mm, wherein the neurotoxin protein is coated onto the high density carrier using techniques commonly known in the art. Ice crystals and gold are preferred carriers of this invention. Ice crystal particles are readily available in average sizes of 0.5 to 2.0 mm in diameter and are thus suited for intracellular delivery. Gold is also a preferred carrier, since gold has a high density and is relatively inert to biological materials and resists oxidation. Moreover, gold is readily available in the form of spheres having an average diameter of from about 0.2 to about 3 mm. In one embodiment, neurotoxin is coated onto ice crystal and/or gold carriers to form drug particles. In a another embodiment, *botulinum* toxin type A is coated onto ice crystals and/or gold carriers to form drug particles to be used in accordance with this invention.

Examples of normally employed "excipients," include pharmaceutical grades of mannitol, sorbitol, inositol, dextrose, sucrose, lactose, trehalose, dextran, starch, cellulose, sodium or calcium phosphates, calcium sulfate, citric acid, tartaric acid, glycine, high molecular weight polyethylene glycols (PEG), and the like and combinations thereof. In one embodiment, the excipient may also include a charged lipid and/or detergent in the pharmaceutical compositions. Suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics, Danbury, Conn.), polyoxyethylenesorbitans, for example, TWEEN® surfactants (Atlas Chemical Industries, Wilmington, Del.), polyoxyethylene ethers, for example, Brij®, pharmaceutically acceptable fatty acid esters, for example, lauryl sulfate and salts thereof (SDS), and the like. Such materials may be used as stabilizers and/or anti-oxidants. Additionally, they may be used to reduce local irritation at the site of administration.

In one broad embodiment, the step of administering a neurotoxin or DNA sequence encoding a neurotoxin according to the present invention may include other steps. These other steps may be carried out before, in conjunction with, and/or after the step of administering the drug particle according to the invention. In one embodiment, these other steps may include applying topical medications, for example aluminum chloride; applying an iontophoresis procedure; and/or administering anticholinergics orally or systemically.

The following examples demonstrate how various conditions may be treated according to the present invention. Although particular doses are described, the dose administered can vary widely according to the severity of the condition and other various subject variables including size, weight, age, and responsiveness to therapy.

The examples also show how a neurotoxin or components thereof may be recombinantly synthesized and reconstituted. The examples relating to recombinant synthesis are substantially similar to the Examples of International Patent Application Publication WO 95/32738, the disclosure of which is incorporated in its entirety herein by reference.

Example 1

Treatment of Post Surgical Myofacial Pain Syndrome

An unfortunate 36 year old woman has a 15 year history of temporomandibular joint disease and chronic pain along the masseter and temporalis muscles. Fifteen years prior to evaluation she noted increased immobility of the jaw associated with pain and jaw opening and closing and tenderness along each side of her face. The left side is originally thought to be worse than the right. She is diagnosed as having temporomandibular joint (TMJ) dysfunction with subluxation of the joint and is treated with surgical orthoplasty meniscusectomy and condyle resection.

She continues to have difficulty with opening and closing her jaw after the surgical procedures and for this reason, several years later, a surgical procedure to replace prosthetic joints on both sides is performed. After the surgical procedure, progressive spasms and deviation of the jaw ensues. Further surgical revision is performed subsequent to the original operation to correct prosthetic joint loosening. The jaw continues to exhibit considerable pain and immobility after these surgical procedures. The TMJ remained tender as well as the muscle itself. There are tender points over the temporomandibular joint as well as increased tone in the entire muscle. She is diagnosed as having post-surgical myofascial pain syndrome and is treated with a needleless injection of 20 U of *botulinum* type A neurotoxin into the skin covering the masseter and temporalis muscles.

Several days after the injections she noted substantial improvement in her pain and reports that her jaw feels looser. This gradually improves over a 2 to 3 week period in which she notes increased ability to open the jaw and diminishing pain. The patient states that the pain is better than at any time in the last 4 years. The improved condition persists for up to 27 months after the original injection of the modified neurotoxin.

Example 2

Peripheral Administration of a Modified Neurotoxin to Treat "Shoulder-Hand Syndrome"

Pain in the shoulder, arm, and hand can develop, with muscular dystrophy, osteoporosis, and fixation of joints.

While most common after coronary insufficiency, this syndrome may occur with cervical osteoarthritis or localized shoulder disease, or after any prolonged illness that requires the patient to remain in bed.

A 46 year old woman presents a shoulder-hand syndrome type pain. The pain is particularly localized at the deltoid region. The patient is treated by a needleless injection of between about 0.05 U/kg to about 2 U/kg of a modified neurotoxin cutaneously to the shoulder, preferably the neurotoxin is *botulinum* type A. The particular dose as well as the frequency of administrations depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 3

Peripheral Administration of a Modified Neurotoxin to Treat Postherpetic Neuralgia Postherpetic neuralgia is one of the most intractable of chronic pain problems. Patients suffering this excruciatingly painful process often are elderly, have debilitating disease, and are not suitable for major interventional procedures. The diagnosis is readily made by the appearance of the healed lesions of herpes and by the patient's history. The pain is intense and emotionally distressing. Postherpetic neuralgia may occur any where, but is most often in the thorax.

A 76 year old man presents a postherpetic type pain. The pain is localized to the abdomen region. The patient is treated by a needleless injection of between about 0.05 U/kg to about 2 U/kg of a modified neurotoxin intradermally to the abdomen, preferably the modified neurotoxin is BoNT/E fused with a leucine-based motif. The particular dose as well as the frequency of administrations depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 4

Peripheral Administration of a Modified Neurotoxin to Treat Inflammatory Pain

A patient, age 45, presents an inflammatory pain in the chest region. The patient is treated by a needleless injection of between about 0.05 U/kg to about 2 U/kg of a *botulinum* neurotoxin type A intramuscularly to the chest. The particular dose as well as the frequency of administrations depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 5

Local Administration of a Neurotoxin to Treat Pain Caused by Bone Fractures

A patient, age 40, suffering from cervical dystonia is treated by an needleless injection of a neurotoxin, preferably *botulinum* toxin type A, at the effected area of the spine. The amount of neurotoxin injected is between about 20 U to about 500 U. The particular dose as well as the frequency of administrations depends upon a variety of factors within the skill of the treating physician, as previously set forth. Within 1-7 days after administration the patient's pain is substantially alleviated. The duration of pain reduction is from about 2 to about 7 months.

Example 6

Treatment of Pain Associated with Muscle Disorder

An unfortunate 36 year old woman has a 15 year history of temporomandibular joint disease and chronic pain along the masseter and temporalis muscles. Fifteen years prior to evaluation she noted increased immobility of the jaw associated with pain and jaw opening and closing and tenderness along each side of her face. The left side is originally thought to be worse than the right. She is diagnosed as having temporomandibular joint (TMJ) dysfunction with subluxation of the joint and is treated with surgical orthoplasty meniscusectomy and condyle resection.

She continues to have difficulty with opening and closing her jaw after the surgical procedures and for this reason, several years later, a surgical procedure to replace prosthetic joints on both sides is performed. After the surgical procedure progressive spasms and deviation of the jaw ensues. Further surgical revision is performed subsequent to the original operation to correct prosthetic joint loosening. The jaw continues to exhibit considerable pain and immobility after these surgical procedures. The TMJ remained tender as well as the muscle itself. There are tender points over the temporomandibular joint as well as increased tone in the entire muscle. She is diagnosed as having post-surgical myofascial pain syndrome and is treated with a needleless injection of 15 U of *botulinum* toxin type A into the masseter and temporalis muscles.

Several days after the injections she noted substantial improvement in her pain and reports that her jaw feels looser. This gradually improves over a 2 to 3 week period in which she notes increased ability to open the jaw and diminishing pain. The patient states that the pain is better than at any time in the last 4 years. The improved condition persists for up to 27 months after the original injection of the modified neurotoxin.

Example 7

Treatment of Pain Subsequent to Spinal Cord Injury

A patient, age 39, experiencing pain spasticity of the right side bicep muscle is treated by needleless injection with about 1.0 U/kg of the modified neurotoxin, preferably the modified neurotoxin is *botulinum* toxin type A. The particular toxin dose and site of injection, as well as the frequency of toxin administrations depend upon a variety of factors within the skill of the treating physician, as previously set forth. Within about 1 to about 7 days after the modified neurotoxin administration, the patient's muscle spasms are substantially reduced. The spasm alleviation persists for up to 27 months.

Example 8

Peripheral Administration of a Modified Neurotoxin to Treat "Shoulder-Hand Syndrome"

A 46 year old woman presents a shoulder-hand syndrome type pain. The pain is particularly localized at the deltoid region. The patient is treated by a needleless injection of between about 0.05 U/kg to about 2 U/kg of *botulinum* type A neurotoxin subcutaneously to the shoulder. The particular dose as well as the frequency of administrations depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 9

Treatment of Axillary Hyperhidrosis

Axillary hyperhidrosis is a condition which may be socially and emotionally disturbing. It is a condition of excessive sweating, which may even cause staining and decaying of clothes. Initially, the treatment usually consists of topical application of antiperspirants containing aluminium salts and/or tanning agents. Iontophoresis using special axillary electrodes are also employed in the treatment of axillary hyperhidrosis. Oral sedatives, tranquilizers or anticholinergic drugs are sometimes used as an adjunct.

If the medical treatment proves ineffective or produces unacceptable side-effect, removal of the axillary sweat glands by surgical excision or liposuction is the other current option. Surgery and liposuction, although often effective in controlling excessive sweating, are commonly complicated by infection, bleeding, scarring, loss of axillary hair, hypoaesthesia, pain due to nerve injury or entrapment and, occasionally, reinnervation of the residual glands and recurrence of hyperhidrosis. Denervation of sweat glands by sympathectomy is also effective but carries the risk of pneumothorax, Homer's syndrome and other complications.

A 35 year old office female dancer presents with a severe case of axillary hyperhidrosis. The area of hyperhidrosis under the forearm is visualized by means of an iodinestarch solution (Minor's iodine-starch test). The hyperhidrosis area is then marked with a pen.

*Botulinum* toxin type A coated on crystal ice particle carrier is loaded into a needleless injector. The projection pressure is set so that the drug particles, i.e., the *botulinum* toxin A coated ice crystal particles, may be delivered to the dermis layer of the skin. Also, such an amount of the drug particle is loaded so that about 20 U to about 60 of *botulinum* toxin type A is delivered to 8×15 cm$^2$ of the demarcated skin area. The particular dose of the neurotoxin and area of injection, as well as the frequency of toxin administrations depend upon a variety of factors to be determined by the treating physician, as previously set forth.

Two weeks after treatment, the axillary sweating response is measured using the Minor's iodine test. The hyperhidrotic area shows about a 95% reduction. The reduction in axillary sweating remains up to about 27 months, preferably 11 months.

Example 10

Treatment of Palmar Hyperhidrosis

*Botulinum* toxin has been injected into the palmar area to treat palmar hyperhidrosis, and has been found to be very effective. However, one of the main drawback of this treatment is the pain cause by the injection. The free nerve endings responsible for the pain sensation occur in the papillary dermis and epidermis whereas the sweat glands are imbedded deep in the dermis and in the upper layer of the subcutaneous tissue. To deliver the *botulinum* toxin as close to the sweat glands as possible, subdermal/subcutaneous injections would be optimal, and presumably less painful than more superficial injections. However, the deeper the injection the greater the risk of causing weakness of the small muscles of the hand and weakening the grip.

A 22 year old concert pianist presents with a palmar hyperhidrosis. The specific area of hyperhidrosis on the hand is visualized by means of an iodinestarch solution (Minor's iodine-starch test). The hyperhidrosis area is then marked with a pen.

*Botulinum* toxin type A coated on crystal ice particle carrier is loaded into a needleless injector. The projection pressure is set so that the drug particles, i.e., the *botulinum* toxin A coated ice crystal particles, may be delivered to the dermis layer of the skin. Also, such amount of the drug particle is loaded so that about 10 U to about 50 U of *botulinum* toxin type A is delivered to 10×15 cm$^2$ of the demarcated skin area. An effective therapeutic dose of *botulinum* toxin is injected without substantial pain. Additionally, no substantial muscle weakness or fatigue of the hand is observed. The particular dose of the neurotoxin and area of injection, as well as the frequency of toxin administrations depend upon a variety of factors to be determined by the treating physician, as previously set forth.

Two weeks after treatment, the reduced sweating response is measured in the area of hyperhidrosis using the Minor's iodine test. The hyperhidrotic area shows about a 95% reduction. The reduction in sweating remains up to about 12 months.

Example 11

Subcloning the BoNT/A-L Chain Gene

This Example describes the methods to clone the polynucleotide sequence encoding the BoNT/A-L chain. The DNA sequence encoding the BoNT/A-L chain is amplified by a PCR protocol that employs synthetic oligonucleotides having the sequences, 5'-AAAGGCCTTTTGTTAATAAACAA-3' (SEQ ID#10) and 5'-GGAATTCTTACTTATTGTATC-CTTTA-3' (SEQ ID#11). Use of these primers allows the introduction of Stu I and EcoR I restriction sites into the 5' and 3' ends of the BoNT/A-L chain gene fragment, respectively. These restriction sites are subsequently used to facilitate unidirectional subcloning of the amplification products. Additionally, these primers introduce a stop codon at the C-terminus of the L chain coding sequence. Chromosomal DNA from *C. botulinum* (strain 63 A) serves as a template in the amplification reaction.

The PCR amplification is performed in a 100 ml volume containing 10 mM Tris-HCl (pH 8.3), 50 mM KCl, 1.5 mM MgCl$_2$, 0.2 mM of each deoxynucleotide triphosphate (dNTP), 50 pmol of each primer, 200 ng of genomic DNA and 2.5 units of Taq-polymerase (Promega). The reaction mixture is patiented to 35 cycles of denaturation (1 minute at 94° C.), annealing (2 minutes at 37° C.) and polymerization (2 minutes at 72° C.). Finally, the reaction is extended for an additional 5 minutes at 72° C.

The PCR amplification product is digested with Stu I and EcoR I, purified by agarose gel electrophoresis, and ligated into Sma I and EcoR I digested pBluescript II SK* to yield the plasmid, pSAL. Bacterial transformants harboring this plasmid are isolated by standard procedures. The identity of the cloned L chain polynucleotide is confirmed by double stranded plasmid sequencing using SEQUENASE (United States Biochemicals) according to the manufacturer's instructions. Synthetic oligonucleotide sequencing primers are prepared as necessary to achieve overlapping sequencing runs. The cloned sequence is found to be identical to the sequence disclosed by Binz, et al., in *J. Biol. Chem.* 265:9153 (1990), and Thompson et al., in *Eur. J. Biochem.* 189:73 (1990).

Site-directed mutants designed to compromise the enzymatic activity of the BoNT/A-L chain can also be created.

Example 12

Expression of the *Botulinum* Toxin Type A-L (BoNt/A-L) Chain Fusion Proteins

This Example describes the methods to verify expression of the wild-type L chains, which may serve as a therapeutic component, in bacteria harboring the pCA-L plasmids. Well isolated bacterial colonies harboring either pCAL are used to inoculate L-broth containing 100 mg/ml ampicillin and 2% (w/v) glucose, and grown overnight with shaking at 30° C. The overnight cultures are diluted 1:10 into fresh L-broth containing 100 mg/ml of ampicillin and incubated for 2 hours. Fusion protein expression is induced by addition of IPTG to a final concentration of 0.1 mM. After an additional 4 hour incubation at 30° C., bacteria are collected by centrifugation at 6,000×g for 10 minutes.

A small-scale SDS-PAGE analysis confirmed the presence of a 90 kDa protein band in samples derived from IPTG-induced bacteria. This $M_r$ is consistent with the predicted size of a fusion protein having MBP (~40 kDa) and BoNT/A-L chain (~50 kDa) components. Furthermore, when compared with samples isolated from control cultures, the IPTG-induced clones contained substantially larger amounts of the fusion protein.

The presence of the desired fusion proteins in IPTG-induced bacterial extracts is also confirmed by Western blotting using the polyclonal anti-L chain probe described by Cenci di Bello et al., in *Eur. J. Biochem.* 219:161 (1993). Reactive bands on PVDF membranes (Pharmacia; Milton Keynes, UK) are visualized using an anti-rabbit immunoglobulin conjugated to horseradish peroxidase (Bio-Rad; Hemel Hempstead, UK) and the ECL detection system (Amersham, UK). Western blotting results confirmed the presence of the dominant fusion protein together with several faint bands corresponding to proteins of lower $M_r$ than the fully sized fusion protein. This observation suggested that limited degradation of the fusion protein occurred in the bacteria or during the isolation procedure. Neither the use of 1 mM nor 10 mM benzamidine (Sigma; Poole, UK) during the isolation procedure eliminated this proteolytic breakdown.

The yield of intact fusion protein isolated by the above procedure remained fully adequate for all procedures described herein. Based on estimates from stained SDS-PAGE gels, the bacterial clones induced with IPTG yielded 5-10 mg of total MBP-wild-type or mutant L chain fusion protein per liter of culture. Thus, the method of producing BoNT/A-L chain fusion proteins disclosed herein is highly efficient, despite any limited proteolysis that did occur.

The MBP-L chain fusion proteins encoded by the pCAL and pCAL-TyrU7 expression plasmids are purified from bacteria by amylose affinity chromatography. Recombinant wild-type or mutant L chains are then separated from the sugar binding domains of the fusion proteins by site-specific cleavage with Factor Xa. This cleavage procedure yielded free MBP, free L chains and a small amount of uncleaved fusion protein. While the resulting L chains present in such mixtures have been shown to possess the desired activities, we have also employed an additional purification step. Accordingly, the mixture of cleavage products is applied to a second amylose affinity column that bound both the MBP and uncleaved fusion protein. Free L chains are not retained on the affinity column, and are isolated for use in experiments described below.

Example 13

Purification of Fusion Proteins and Isolation of Recombinant BoNT/A-L Chains

This Example describes a method to produce and purify wild-type recombinant BoNT/A light chains from bacterial clones. Pellets from 1 liter cultures of bacteria expressing the wild-type BoNT/A-L chain proteins are resuspended in column buffer [10 mM Tris-HCl (pH 8.0), 200 mM NaCl, 1 mM EGTA and 1 mM DTT] containing 1 mM phenyl-methane-sulfonyl fluoride (PMSF) and 10 mM benzamidine, and lysed by sonication. The lysates are cleared by centrifugation at 15,000×g for 15 minutes at 4° C. Supernatants are applied to an amylose affinity column [2×10 cm, 30 ml resin] (New England BioLabs; Hitchin, UK). Unbound proteins are washed from the resin with column buffer until the eluate is free of protein as judged by a stable absorbance reading at 280 nm. The bound MBP-L chain fusion protein is subsequently eluted with column buffer containing 10 mM maltose. Fractions containing the fusion protein are pooled and dialyzed against 20 mM Tris-HCl (pH 8.0) supplemented with 150 mM NaCl, 2 mM, $CaCl_2$ and 1 mM DTT for 72 hours at 4° C.

Fusion proteins are cleaved with Factor $X_2$ (Promega; Southampton, UK) at an enzyme:substrate ratio of 1:100 while dialyzing against a buffer of 20 mM Tris-HCl (pH 8.0) supplemented with 150 mM NaCl, 2 mM, $CaCl_2$ and 1 mM DTT. Dialysis is carried out for 24 hours at 4° C. The mixture of MBP and either wild-type or mutant L chain that resulted from the cleavage step is loaded onto a 10 ml amylose column equilibrated with column buffer. Aliquots of the flow through fractions are prepared for SDS-PAGE analysis to identify samples containing the L chains. Remaining portions of the flow through fractions are stored at −20° C. Total *E. coli* extract or the purified proteins are solubilized in SDS sample buffer and patiented to PAGE according to standard procedures. Results of this procedure indicated the recombinant toxin fragment accounted for roughly 90% of the protein content of the sample.

The foregoing results indicates that the approach to creating MBP-L chain fusion proteins described herein could be used to efficiently produce wild-type and mutant recombinant BoNT/A-L chains. Further, the results demonstrate that recombinant L chains could be separated from the maltose binding domains of the fusion proteins and purified thereafter.

A sensitive antibody-based assay is developed to compare the enzymatic activities of recombinant L chain products and their native counterparts. The assay employed an antibody having specificity for the intact C-terminal region of SNAP-25 that corresponded to the BoNT/A cleavage site. Western Blotting of the reaction products of BoNT/A cleavage of SNAP-25 indicated an inability of the antibody to bind SNAP-25 sub-fragments. Thus, the antibody reagent employed in the following Example detected only intact SNAP-25. The loss of antibody binding served as an indicator of SNAP-25 proteolysis mediated by added BoNT/A light chain or recombinant derivatives thereof.

Example 14

Evaluation of the Proteolytic Activities of Recombinant L Chains Against a SNAP-25 Substrate This Example describes a method to demonstrate that both native and recombinant BoNT/A-L chains can proteolyze a SNAP-25 substrate. A quantitative assay is employed to compare the abilities of the wild-type and their recombinant analogs to cleave a SNAP-25 substrate. The substrate utilized for this assay is obtained by preparing a glutathione-S-transferase (GST)-SNAP-25 fusion protein, containing a cleavage site for thrombin, expressed using the pGEX-2T vector and purified by affinity chromatography on glutathione agarose. The SNAP-25 is then cleaved from the fusion protein using thrombin in 50 mM Tris-HCl (pH 7.5) containing 150 mM NaCl and 2.5 mM $CaCl_2$ (Smith et al., Gene 67:31 (1988)) at an enzyme:substrate ratio of 1:100. Uncleaved fusion protein and the cleaved glutathione-binding domain bound to the gel. The recombinant SNAP-25 protein is eluted with the latter buffer and dialyzed against 100 mM HEPES (pH 7.5) for 24 hours at 4° C. The total protein concentration is determined by routine methods.

Rabbit polyclonal antibodies specific for the C-terminal region of SNAP-25 are raised against a synthetic peptide having the amino acid sequence, CANQRATKMLGSG (SEQ ID#12). This peptide corresponded to residues 195 to 206 of the synaptic plasma membrane protein and an N-terminal cysteine residue not found in native SNAP-25. The synthetic peptide is conjugated to bovine serum albumin (BSA) (Sigma; Poole, UK) using maleimidobenzoyl-N-hydroxysuccinimide ester (MBS) as a cross-linking agent (Sigma; Poole, UK) to improve antigenicity (Liu et al., Biochemistry 18:690 (1979) 1. Affinity purification of the anti-peptide antibodies is carried out using a column having the antigenic peptide conjugated via its N-terminal cysteine residue to an aminoalkyl agarose resin (Bio-Rad; Hemel Hempstead, UK), activated with iodoacetic acid using the cross-linker ethyl 3-(3-dimethylpropyl)carbodiimide. After successive washes of the column with a buffer containing 25 mM Tris-HCl (pH 7.4) and 150 mM NaCl, the peptide-specific antibodies are eluted using a solution of 100 mM glycine (pH 2.5) and 200 mM NaCl, and collected in tubes containing 0.2 ml of 1 M Tris-HCl (pH 8.0) neutralizing buffer.

All recombinant preparations containing wild-type L chain are dialyzed overnight at 4° C. into 100 mM HEPES (pH 7.5) containing 0.02% Lubrol and 10 mM zinc acetate before assessing their enzymatic activities. BoNT/A, previously reduced with 20 mM DTT for 30 minutes at 37° C., as well as these dialyzed samples, are then diluted to different concentrations in the latter HEPES buffer supplemented with 1 mM DTT.

Reaction mixtures include 5 ml recombinant SNAP-25 substrate (8.5 mM final concentration) and either 20 ml reduced BoNT/A or recombinant wild-type L chain. All samples are incubated at 37° C. for 1 hour before quenching the reactions with 25 ml aqueous 2% trifluoroacetic acid (TFA) and 5 mM EDTA (Foran et al., Biochemistry 33:15365 (1994)). Aliquots of each sample are prepared for SDS-PAGE and Western blotting with the polyclonal SNAP-25 antibody by adding SDS-PAGE sample buffer and boiling. Anti-SNAP-25 antibody reactivity is monitored using an ECL detection system and quantified by densitometric scanning.

Western blotting results indicate clear differences between the proteolytic activities of the purified mutant L chain and either native or recombinant wild-type BoNT/A-L chain. Specifically, recombinant wild-type L chain cleaves the SNAP-25 substrate, though somewhat less efficiently than the reduced BoNT/A native L chain that serves as the positive control in the procedure. Thus, an enzymatically active form of the BoNT/A-L chain is produced by recombinant means and subsequently isolated. Moreover, substitution of a single amino acid in the L chain protein abrogated the ability of the recombinant protein to degrade the synaptic terminal protein.

As a preliminary test of the biological activity of the wild-type recombinant BoNT/A-L chain, the ability of the MBP-L chain fusion protein to diminish $Ca^{2+}$-evoked catecholamine release from digitonin-permeabilized bovine adrenochromaffin cells is examined. Consistently, wild-type recombinant L chain fusion protein, either intact or cleaved with Factor $X_2$ to produce a mixture containing free MBP and recombinant L chain, induced a dose-dependent inhibition of $Ca^{2+}$-stimulated release equivalent to the inhibition caused by native BoNT/A.

Example 15

Reconstitution of Native L Chain, Recombinant Wild-Type L Chain with Purified H Chain Native H and L chains are dissociated from BoNT/A (List Biologicals Inc.; Campbell, USA) with 2 M urea, reduced with 100 mM DTT and then purified according to established chromatographic procedures (Kozaki et al., Japan J. Med. Sci. Biol. 34:61 (1981); Maisey et al., Eur. J. Biochem. 177: 683 (1988)). Purified H chain is combined with an equimolar amount of either native L chain or recombinant wild-type L chain. Reconstitution is carried out by dialyzing the samples against a buffer consisting of 25 mM Tris (pH 8.0), 50 mM zinc acetate and 150 mM NaCl over 4 days at 4° C. Following dialysis, the association of the recombinant L chain and native H chain to form disulfide-linked 150 kDa di-chains is monitored by SDS-PAGE and quantified by densitometric scanning. The proportion of di-chain molecules formed with the recombinant L chains is lower than that obtained when native L chain is employed. Indeed, only about 30% of the recombinant wild-type or mutant L chain is reconstituted while >90% of the native L chain reassociated with the H chain. In spite of this lower efficiency of reconstitution, sufficient material incorporating the recombinant L chains is easily produced for use in subsequent functional studies.

Example 16

A Study of Botulinum Neurotoxin Type A Activity when the Toxin is Produced in Skin and Muscle Cells of an Animal Genes encoding botulinum toxin type A are expressed in the skin and muscle cells of live mice in situ by needleless injection of DNA coated microprojectiles into the tissues.

The DNA encoding recombinant botulinum toxin comprises two nucleotide sequences. One sequence contains a human beta-actin promoter fused to a DNA sequence encoding the heavy chain of botulinum type A. The second sequence contains a human beta-actin promoter fused to a DNA sequence encoding a light chain of botulinum toxin. Polyadenylation signal sequences are added 3' to the Clostridium genes. Stop codons are placed at the 5' end of each gene to allow translation of the complete heavy chain and light chains.

Substance particles, for example, gold particles or tungsten particles, having a range of diameter from 1 to 3 micrometers or 2 to 5 micrometers are coated with DNA by mixing sequentially 25 microliters of gold or tungsten microprojectiles in an aqueous slurry, 2.5 microliters of DNA (1 mg/ml), 25 microliters of $CaCl_2$ and 5 microliters of free base spermidine (1M). After 10 min of incubation, the microprojectiles are collected by centrifugation and the supernatant removed. The pellet is washed once in 70% ethanol, centrifuged and resuspended in 25 microliters of 100% ethanol. The ethanol is allowed to evaporate from the DNA coated microprojectiles before injection.

The DNA coated microprojectiles are administered into the skin, or into the skin and underlying muscle tissue of the mice by needleless injection.

*Botulinum* toxin gene expression is assessed by, for example, in situ hybridization. In situ hybridization is performed 24 hours after the injection. The muscle and skin tissues are frozen and cryosectioned at 10-micrometer thickness. The sections are dried onto gelatin/chrom alum-coated slides, fixed with 4% paraformaldehyde and hybridized with $^{35}$S-labeled synthetic oligonucleotide probes complementary to the *botulinum* toxin mRNAs. FITC labeled antibodies to the heavy and light chains were also used as probes. Results showed 10 to 20% of the skin cells in the area of injection expressed the *botulinum* toxin genes. While 5 to 10% of the muscle cells in the injection area expressed the genes.

In mice where the DNA coated particles were administered to the skin and substantially to underlying muscle tissue, a partial paralysis of the effected muscle was noted.

Example 17

Peripheral Administration of a Modified Neurotoxin DNA Encoding Sequence to Treat Inflammatory Pain A patient, age 45, presents a case of blepharospasm. The patient is treated by a needleless injection to the skin near the eye of between about 10 nanograms to about 5 micrograms of DNA encoding *botulinum* neurotoxin plus appropriate flanking sequences, preferably the neurotoxin is type A. Preferably, gold or tungsten microprojectiles are coated with the DNA. The particular dose as well as the frequency of administration depends upon a variety of factors within the skill of the treating physician. Within 1-7 days after modified neurotoxin administration the patient's pain is substantially alleviated. The duration of the alleviation of spasmotic winking is from about 7 to about 27 months.

Example 18

Treatment of Gustatory Sweating

Gustatory sweating (Frey's syndrome, auriculotemporal syndrome) is sweating of the facial skin during meals and commonly is seen following parotid gland surgery and trauma to the preauricular region. Denervated sweat glands become reinnervated by misdirected sprouting of parasympathetic secretomotor fibers that have lost their "target organ," the salivary gland. Gustatory sweating is experienced by 13-50% of patients after pariodectomy.

A 40 year old man presents a classic case of Frey's syndrome. The area of hyperhydrosis on the face is visualized by means of an iodinestarch solution (Minor's iodine-starch test) after sweating is stimulated by having the patient chew an apple or sour fruit candy. The hyperhidrosis area is then marked with a pen.

DNA encoding *botulinum* toxin type A and appropriate flanking sequences, i.e. transcription initiation and termination sequences, is coated on a gold particle carrier. The coated carrier is loaded into a needleless injector. The projection pressure is set so that the drug particles may be delivered to the dermis layer of the skin. The particular dose of the neurotoxin DNA and area of injection, as well as the frequency of toxin administration depends upon a variety of factors to be determined by the treating physician, as previously set forth.

Seven days after treatment, the gustatory sweating is measured using the Minor's iodine test. The hyperhidrotic area shows about 93% reduction. The reduction in gustatory sweating starts after about 72 hours and persists up to about 12 months.

While this invention has been described with respect to various specific examples and embodiments, it is to be understood that the invention is not limited thereto and that it can be variously practiced with the scope of the following claims. Other embodiments, versions, and modifications within the scope of the present invention are possible.

What is claimed is:

1. A method for treating a condition in a patient in need thereof, the method comprising the step of locally administering a therapeutically effective amount of a *botulinum* toxin in powder form to the patient using a needleless injector, wherein the condition is selected from the group consisting of spasmodic dysphonia, laryngeal dystonia, oromandibular dysphonia, lingual dystonia, cervical dystonia, focal hand dystonia, blepharospasm, strabismus, hemifacial spasm, eyelid disorder, cerebral palsy, focal spasticity, spasmodic colitis, neurogenic bladder, anismus, limb spasticity, tics, tremors, bruxism, anal fissure, achalasia, fibromyalgia, dysphagia, lacrimation, hyperhydrosis, excessive salivation, excessive gastrointestinal secretions, excessive mucous secretion, pain from muscle spasms, headache pain, brow furrows and skin wrinkles, whereby a symptom of the condition is thereby alleviated within 1 to 7 days.

2. The method of claim 1 wherein duration of alleviation is provided that lasts from about 7 to about 27 months.

3. The method of claim 1 wherein the *botulinum* toxin is *botulinum* toxin type A and the therapeutically effective amount administered to the patient is between about 0.05 U/kg to about 2 U/kg.

4. A method for treating a condition in a patient in need thereof, the method comprising the step of locally administering a therapeutically effective amount of a *botulinum* toxin type A or B in powder form to the patient using a needleless injector, wherein the condition is selected from the group consisting of spasmodic dysphonia, laryngeal dystonia, oromandibular dysphonia, lingual dystonia, cervical dystonia, focal hand dystonia, blepharospasm, strabismus, hemifacial spasm, eyelid disorder, cerebral palsy, focal spasticity, spasmodic colitis, neurogenic bladder, anismus, limb spasticity, tics, tremors, bruxism, anal fissure, achalasia, fibromyalgia, dysphagia, lacrimation, hyperhydrosis, excessive salivation, excessive gastrointestinal secretions, excessive mucous secretion, pain from muscle spasms, headache pain, brow furrows and skin wrinkles, whereby a symptom of the condition is thereby alleviated.

5. The method of claim 4 wherein the *botulinum* toxin is administered with a carrier made of a solid material.

6. The method of claim 5, wherein the carrier is less than 10 millimeters in diameter.

7. The method of claim 6, wherein the solid material is selected from the group consisting of gold, platinum, tungsten and an ice crystal.

* * * * *

UNITED STATES PATENT AND TRADEMARK OFFICE
CERTIFICATE OF CORRECTION

PATENT NO.         : 8,025,889 B2
APPLICATION NO.    : 12/340150
DATED              : June 15, 2010
INVENTOR(S)        : Patricia S. Walker It is certified that error appears in the above-identified patent and that said Letters Patent is hereby corrected as shown below:

Title Page, item (56):

On page 2, in column 1, under "Other Publications", line 29, delete "Artroscopy" and insert -- Arthroscopy --, therefor.

On page 2, in column 2, under "Other Publications", line 6, delete "Neruolbiol." and insert -- Neurolbiol. --, therefor.

On page 2, in column 2, under "Other Publications", line 22, delete "Eveoked" and insert -- Evoked --, therefor.

On page 2, in column 2, under "Other Publications", line 31, delete "Regulared" and insert -- Regulated --, therefor.

In column 5, line 14, delete "norepinephine." and insert -- norepinephrine. --, therefor.

In column 6, line 49, after "needles" insert -- . --.

In column 7, line 66, delete "tetanti" and insert -- tetani --, therefor.

In column 8, line 47, delete "tetnus" and insert -- tetanus --, therefor.

In column 9, line 27, delete "tetanti" and insert -- tetani --, therefor.

In column 16, line 24, delete "Myofacial" and insert -- Myofascial --, therefor.

In column 21, line 16, delete "pCA-L" and insert -- pCAL --, therefor.

In column 25, line 38, delete "spasmotic" and insert -- spasmodic --, therefor.

Signed and Sealed this
Twentieth Day of March, 2012

David J. Kappos
*Director of the United States Patent and Trademark Office*

SEQUENCE LISTING

```
<160> NUMBER OF SEQ ID NOS: 12

<210> SEQ ID NO 1
<211> LENGTH: 3891
<212> TYPE: DNA
<213> ORGANISM: botulinum toxin

<400> SEQUENCE: 1
atgcaatttg ttaataaaca atttaattat aaagatcctg taaatggtgt tgatattgct      60
tatataaaaa ttccaaatgt aggacaaatg caaccagtaa aagcttttaa aattcataat     120
aaaatatggg ttattccaga aagagataca tttacaaatc ctgaagaagg agatttaaat     180
ccaccaccag aagcaaaaca agttccagtt tcatattatg attcaacata tttaagtaca     240
gataatgaaa aagataatta tttaaaggga gttacaaaat tatttgagag aatttattca     300
actgatcttg gaagaatgtt gttaacatca atagtaaggg gaataccatt ttggggtgga     360
agtacaatag atacagaatt aaaagttatt gatactaatt gtattaatgt gatacaacca     420
gatggtagtt atagatcaga agaacttaat ctagtaataa taggaccctc agctgatatt     480
atacagtttg aatgtaaaag ctttggacat gaagttttga atcttacgcg aaatggttat     540
```

```
ggctctactc aatacattag atttagccca gattttacat ttggttttga ggagtcactt    600
gaagttgata caaatcctct tttaggtgca ggcaaatttg ctacagatcc agcagtaaca    660
ttagcacatg aacttataca tgctggacat agattatatg aatagcaat taatccaaat    720
agggttttta agtaaatac taatgcctat tatgaaatga gtgggttaga agtaagcttt    780
gaggaactta gaacatttgg gggacatgat gcaaagttta tagatagttt acaggaaaac    840
gaatttcgtc tatattatta taataagttt aaagatatag caagtacact aataaaagct    900
aaatcaatag taggtactac tgcttcatta cagtatatga aaaatgtttt taaagagaaa    960
tatctcctat ctgaagatac atctggaaaa ttttcggtag ataaattaaa atttgataag   1020
ttatagaaaa tgttaacaga gattagaca gaggataatt ttgttaagtt ttttaaagta   1080
cttaacagaa aaacatattt gaattttgat aaagccgtat ttaagataaa tatagtacct   1140
aaggtaaatt acacaatata tgatggattt aatttaagaa atacaaattt agcagcaaac   1200
tttaatggtc aaaatacaga aattaataat atgaattta ctaaactaaa aaattttact   1260
ggattgtttg aattttataa gttgctatgt gtaagaggga taataacttc taaaactaaa   1320
tcattagata aaggatacaa taaggcatta aatgatttat gtatcaaagt taataattgg   1380
gacttgtttt ttagtccttc agaagataat tttactaatg atctaaataa aggagaagaa   1440
attacatctg atactaatat agaagcagca gaagaaaata ttagtttaga tttaatacaa   1500
caatattatt aacctttaa ttttgataat gaacctgaaa atatttcaat agaaaatctt   1560
tcaagtgaca ttataggcca attagaactt atgcctaata tagaaagatt tcctaatgga   1620
aaaagtatg agttagataa atatactatg ttccattatc ttcgtgctca agaatttgaa   1680
catggtaaat ctaggattgc tttaacaaat tctgttaacg aagcattatt aaatcctagt   1740
cgtgtttata cattttttc ttcagactat gtaaagaaag ttaataaagc tacggaggca   1800
gctatgtttt taggctgggt agaacaatta gtatatgatt ttaccgatga aactagcgaa   1860
gtaagtacta cggataaaat tgcggatata actataatta ttccatatat aggacctgct   1920
ttaaatatag gtaatatgtt atataaagat gattttgtag gtgctttaat attttcagga   1980
gctgttattc tgttagaatt tataccagag attgcaaatac ctgtattagg tacttttgca   2040
cttgtatcat atattgcgaa taaggttcta accgttcaaa caatagataa tgctttaagt   2100
aaaagaaatg aaaaatggga tgaggtctat aaatatatag taacaaattg gttagcaaag   2160
gttaatacac agattgatct aataagaaaa aaaatgaaag aagctttaga aaatcaagca   2220
gaagcaacaa aggctataat aaactatcag tataatcaat atactgagga agagaaaaat   2280
aatattaatt ttaatattga tgatttaagt tcgaaactta atgagtctat aaataaagct   2340
atgattaata taaataaatt tttgaatcaa tgctctgttt catattaat gaattctatg   2400
atcccttatg gtgttaaacg gttagaagat tttgatgcta gtcttaaaga tgcattatta   2460
aagtatatat atgataatag aggaactta attggtcaag tagatagatt aaaagataaa   2520
gttaataata cacttagtac agatatacct tttcagcttt ccaaataggt agataatcaa   2580
agattattat ctacatttac tgaatatatt aagaatatta ttaatacttc tatattgaat   2640
ttaagatatg aaagtaatca tttaatagac ttatctaggt atgcatcaaa aataaatatt   2700
ggtagtaaag taaattttga tccaatagat aaaaatcaaa ttcaattatt taatttagaa   2760
agtagtaaaa ttgaggtaat tttaaaaaat gctattgtat ataatagtat gtatgaaaat   2820
tttagtacta gcttttggat aagaattcct aagtatttta acagtataag tctaaataat   2880
gaatatacaa taataaattg tatggaaaat aattcaggat ggaaagtatc acttaattat   2940
```

```
ggtgaaataa tctggacttt acaggatact caggaaataa acaaagagt agttttaaa    3000
tagagtcaaa tgattaatat atcagattat ataaacagat ggattttgt aactatcact   3060
aataatagat taaataactc taaaatttat ataaatggaa gattaataga tgaaaaacca   3120
atttcaaatt taggtaatat tcatgctagt aataatataa tgtttaaatt agatggttgt   3180
agagatacac atagatatat ttggataaaa tattttaatc ttttttgataa ggaattaaat  3240
gaaaagaaa tcaagatttt atatgataat caatcaaatt caggtatttt aaaagacttt    3300
tggggtgatt atttacaata tgataaaacca tagtatatgt taaatttata tgatccaaat  3360
aaatatgtcg atgtaaataa tgtaggtatt agaggttata tgtatcttaa agggcctaga   3420
ggtagcgtaa tgactacaaa catttatttta aattcaagtt tgtatagggg gacaaaattt  3480
attataaaaa aatatgcttc tggaaataaa gataatattg ttagaaataa tgatcgtgta   3540
tatattaatg tagtagttaa aaataaagaa tataggttag ctactaatgc atcacaggca   3600
ggcgtagaaa aaatactaag tgcattagaa atacctgatg taggaaatct aagtcaagta   3660
gtagtaatga agtcaaaaaa tgatcaagga ataacaaata aatgcaaaat gaatttacaa   3720
gataataatg ggaatgatat aggctttata ggatttcatc agtttaataa tatagctaaa   3780
ctagtagcaa gtaattggta taatagacaa atagaaagat ctagtaggac tttgggttgc   3840
tcatgggaat ttattcctgt agatgatgga tggggagaaa ggccactgta a            3891
```

```
<210> SEQ ID NO 2
<211> LENGTH: 3876
<212> TYPE: DNA
<213> ORGANISM: botulinum toxin

<400> SEQUENCE: 2
atgccagtta caataaataa tttaattat aatgatccta ttgataatga caatattatt      60
atgatggaac ctccatttgc aaggggtacg gggagatatt ataaagcttt taaaatcaca    120
gatcgtattt ggataatacc cgaaagatat acttttggat ataaacctga ggattttaat   180
aaaagttccg gtatttttaa tagagatgtt tgtgaatatt atgatccaga ttacttaaat   240
accaatgata aaaagaatat attttttccaa acattgatca agttatttaa tagaatcaaa    300
tcaaaaccat ggggtgaaaa gttattagag atgattataa atggtatacc ttatcttgga    360
gatagacgtg ttccactcga agagtttaac acaaacattg ctagtgtaac tgttaataaa    420
ttaattagta atccaggaga agtggagcga aaaaaaggta ttttcgcaaa tttaataata    480
tttgaccctg gccagttttt aaatgaaaat gagactatag atataggtat acaaaaatcat   540
tttgcatcaa gggaaggctt tggggggtata atgcaaatga attttgtcc agaatatgta    600
agcgtattta taatgttca agaaaacaaa ggcgcaagta tatttaatag acgtggatat     660
ttttcagatc cagccttgat attaatgcat gaacttatac atgttttgca tggattatat    720
ggcattaaag tagatgattt accaattgta ccaaatgaaa aaaaatttt tatgcaatct    780
acagatacta tacaggcaga agaactatat acatttggag acaagatcc cagcatcata    840
tctccttcta cagataaaag tatctatgat aaagttttgc aaaattttag ggggatagtt    900
gatagactta caaggttttt agtttgcata tcagatccta acattaacat taatatatat    960
aaaaatataat ttaagataaa atataaaatc gttgaagatt ctgaaggaaa atatagtata  1020
gatgtagaaa gtttcaataa attatataaa agcttaatgt taggttttac agaaattaat  1080
atagcagaaa attataaaat aaaaactaga gcttcttatt ttagtgattc cttaccacca   1140
gtaaaaataa aaatttatt agataatgaa atctatacta tagaggaagg gtttaatata   1200
```

```
tctgataaaa atatgggaaa agaatatagg ggtcagaata aagctataaa taaacaagct    1260
tatgaagaaa tcagcaagga gcatttggct gtatataaga tacaaatgtg taaaagtgtt    1320
aaagttccag gaatatgtat tgatgtcgat aatgaaaatt tgttctttat agctgataaa    1380
aatagttttt cagatgattt atctaaaaat gaaagagtag aatataatac acagaataat    1440
tatataggaa atgactttcc tataaatgaa ttaattttag atactgattt aataagtaaa    1500
atagaattac aagtgaaaaa tacagaatca cttactgatt ttaatgtaga tgttccagta    1560
tatgaaaaac aacccgctat aaaaaaagtt tttacagatg aaaataccat ctttcaatat    1620
ttatactctc agacatttcc tctaaatata agagatataa gtttaacatc ttcatttgat    1680
gatgcattat tagtttctag caaagtttat tcatttttt ctatggatta tattaaaact    1740
gctaataaag tagtagaagc aggattattt gcaggttggg tgaaacagat agtagatgat    1800
tttgtaatcg aagctaataa aagcagtact atggataaaa ttgcagatat atctctaatt    1860
gttccttata taggattagc tttaaatgta ggagatgaaa cagctaaagg aaattttgaa    1920
agtgcttttg agattgcagg atccagtatt ttactagaat ttataccaga acttttaata    1980
cctgtagttg gagtcttttt attagaatca tatattgaca ataaaaataa aattattaaa    2040
acaatagata atgctttaac taaaagagtg gaaaaatgga ttgatatgta gggattaata    2100
gtagcgcaat ggctctcaac agttaatact caatttttata caataaaaga gggaatgtat    2160
aaggctttaa attatcaagc acaagcattg gaagaaataa taaaatacaa atataatata    2220
tattctgaag aggaaaagtc aaatattaac atcaatttta atgatataaa ttctaaactt    2280
aatgatggta ttaaccaagc tatggataat ataaatgatt ttataaatga atgttctgta    2340
tcatatttaa tgaaaaaaat gattccatta gctgtaaaaa aattactaga ctttgataat    2400
actctcaaaa aaaatttatt aaattatata gatgaaaata aattatattt aattggaagt    2460
gtagaagatg aaaaatcaaa agtagataaa tacttgaaaa ccattatacc atttgatctt    2520
tcaacgtatt ctaatattga aatactaata aaaatatttta ataaatataa tagcgaaatt    2580
ttaaataata ttatcttaaa tttaagatat agagataata atttaataga tttatcagga    2640
tatggagcaa aggtagaggt atatgatggg gtcaagctta atgataaaaa tcaatttaaa    2700
ttaactagtt cagcagatag taagattaga gtcactcaaa atcagaatat tatatttaat    2760
agtatgttcc ttgattttag cgttagcttt tggataagga tacctaaaata taggaatgat    2820 gatatacaaa attatattca taatgaatat acgataatta attgtatgaa aaataattca    2880
ggctggaaaa tatctattag gggtaatagg ataaatatgga ccttaattga tataaatgga    2940
aaaaccaaat cagtattttt tgaatataac ataagagaag atatatcaga gtatataaat    3000
agatggtttt ttgtaactat tactaataat ttggataatg ctaaaattta tattaatggc    3060
acgttagaat caaatatgga tattaaagat ataggagaag ttattgttaa tggtgaaata    3120
acatttaaat tagatggtga tgtagataga acacaattta tttggatgaa atattttagt    3180 attttttaata cgcaattaaa tcaatcaaat attaaagaga tatataaaat tcaatcatat    3240
agcgaatagt taaagatttt ttgggaaaat cctttaatgt ataataaaga atattatatg    3300
tttaatgcgg ggaataaaaa ttcatatatt aaactagtga aagattcatc tgtaggtgaa    3360
atattaatac gtagcaaata taatcagaat tccaattata taaattatag aaatttatat    3420
attggagaaa aatttattat aagaagagag tcaaattctc aatctataaa tgatgatata    3480
gttagaaaag aagattatat acatctagat ttggtacttc accatgaaga gtggagagta    3540
tatgcctata aatattttaa ggaacaggaa gaaaaattgt ttttatctat tataagtgat    3600
```

-continued

| | |
|---|---|
| tctaatgaat tttataagac tatagaaata aaagaatatg atgaacagcc atcatatagt | 3660 |
| tgtcagttgc ttttaaaaa agatgaagaa agtactgatg atataggatt gattggtatt | 3720 |
| catcgtttct aggaatctgg agttttacgt aaaaagtata aagattattt ttgtataagt | 3780 |
| aaatggtagt taaagaggt aaaaaggaaa ccatataagt caaatttggg atgtaattgg | 3840 |
| cagtttattc ctaaagatga agggtggact gaataa | 3876 |

<210> SEQ ID NO 3
<211> LENGTH: 3876
<212> TYPE: DNA
<213> ORGANISM: botulinum toxin

<400> SEQUENCE: 3

| | |
|---|---|
| atgccagtta caataaataa ttttaattat aatgatccta ttgataataa taatattatt | 60 |
| atgatggagc ctccatttgc gagaggtacg gggagatatt ataaagcttt taaaatcaca | 120 |
| gatcgtattt ggataatacc ggaaagatat acttttggat ataaacctga ggatttttaat | 180 |
| aaaagttccg gtatttttaa tagagatgtt tgtgaatatt atgatccaga ttagttaaat | 240 |
| actaatgata aaagaatat attttttacaa acaatgatca agttatttaa tagaatcaaa | 300 |
| tcaaaaccat tgggtgaaaa gttattagag atgattataa atggtatacc ttatcttgga | 360 |
| gatagacgtg ttccactcga agagtttaac acaaacattg ctagtgtaac tgttaataaa | 420 |
| ttaatcagta atccaggaga agtggagcga aaaaaaggta ttttcgcaaa tttaataata | 480 |
| tttggacctg ggccagtttt aaatgaaaat gagactatag atagggtat acaaaatcat | 540 |
| tttgcatcaa gggaaggctt cggggggtata atgcaaatga gttttgccc agaatatgta | 600 |
| agcgtatttta ataatgttca agaaaacaaa ggcgcaagta tatttaatag acgtggatat | 660 |
| ttttcagatc cagccttgat attaatgcat gaacttatac atgttttaca tggattatat | 720 |
| ggcattaaag tagatgattt accaattgta ccaaatgaaa aaaaattttt tatgcaatct | 780 |
| acagatgcta tacaggcaga agaactatat acatttggag acaagatcc cagcatcata | 840 |
| actccttcta cggataaaag tatctatgat aaagttttgc aaaattttag agggatagtt | 900 |
| gatagactta acaaggtttt agtttgcata tcagatccta acattaatat taatatatat | 960 |
| aaaaataaat ttaagataa atataaattc gttgaagatt ctgagggaaa atatagtata | 1020 |
| gatgtagaaa gttttgataa attatataaa agcttaatgt ttggttttac agaaactaat | 1080 |
| atagcagaaa attataaaat aaaaactaga gcttcttatt ttagtgattc cttaccacca | 1140 |
| gtaaaaataa aaaatttatt agataatgaa atctatacta gaggaaagg ttttaatata | 1200 |
| tctgataaag atatggaaaa agaatataga ggtcagaata agctataaaa taaacaagct | 1260 |
| tatgaagaaa ttagcaagga gcatttggct gtatataaga tacaaatgtg taaaagtgtt | 1320 |
| aaagctccag gaatatgtat tgatgttgat aatgaagatt tgttctttat agctgataaa | 1380 |
| aatagttttt cagatgattt atctaaaaac gaaagaatag aatataatac acagagtaat | 1440 |
| tatatagaaa atgacttccc tataaatgaa ttaatttag atactgatttt aataagtaaa | 1500 |
| atagaattac aagtgaaaaa tacagaatca cttactgatt ttaatgtaga tgttccagta | 1560 |
| tatgaaaaac aacccgctat aaaaaaaatt tttacagatg aaaataccat ctttcaatat | 1620 |
| ttatagtctc agacatttct cttagatata agagatataa gtttaacatc ttcatttgat | 1680 |
| gatgcattat tattttctaa caaagtttat tcatttttt ctatggatta tattaaaact | 1740 |
| gctaataaag tggtagaagc aggattattt gcaggttggg tgaaacagat agtaaatgat | 1800 |
| tttgtaatcg aagctaataa aagcaatact atggataaaa ttgcagatat atctctaatt | 1860 |

```
gttccttata taggattagc tttaaatgta ggaaatgaaa cagctaaagg aaattttgaa    1920
aatgcttttg agattgcagg agccagtatt ctactagaat ttataccaga acttttaata    1980
cctgtagttg gagcctttt attagaatca tatattgaca ataaaaataa aattattaaa    2040
acaatagata atgctttaac taaaagaaat gaaaaatgga gtgatatgta gggattaata    2100
gtagcgcaat ggctctcaac agttaatact caattttata caataaaaga gggaatgtat    2160
aaggctttaa attatcaagc acaagcattg gaagaaataa taaaatacag atataatata    2220
tattctgaaa agaaaagtc aaatattaac atcgatttta atgatataaa ttctaaactt    2280
aatgagggta ttaaccaagc tatagataat ataaataatt ttataaatgg atgttctgta    2340
tcatatttaa tgaaaaaaat gattccatta gctgtagaaa aattactaga ctttgataat    2400
actctcaaaa aaatttgtt aaattatata gatgaaaata aattatattt gattggaagt    2460
gcagaatatg aaaaatcaaa agtaaataaa tagttgaaaa ccattatgcc gtttgatctt    2520
tcaatatata ccaatgatac aatactaata gaaatgttta ataaatataa tagcgaaatt    2580
ttaaataata ttatcttaaa tttaagatat aaggataata atttaataga tttatcagga    2640 tatgggcaa aggtagaggt atatgatgga gtcgagctta atgataaaaa tcaatttaaa    2700
ttaactagtt cagcaaatag taagattaga gtgactcaaa atcagaatat catatttaat    2760
agtgtgttcc ttgattttag cgttagctt tggataagaa tacctaaaata taagaatgat    2820 ggtatacaaa attatattca taatgaatat acaataatta attgtatgaa aaataattcg    2880
ggctggaaaa tatctattag gggtaatagg ataatatgga ctttaattga tataaatgga    2940
aaaaccaaat cggtatttt tgaatataac ataagagaag atatatcaga gtatataaat    3000
agatggtttt ttgtaactat tactaataat ttgaataacg ctaaaatta tattaatggt    3060 aagctagaat caaatacaga tattaaagat ataagagaag ttattgctaa tggtgaaata    3120
atatttaaat tagatggtga tatagataga acacaatta tttggatgaa atattcagt    3180 atttttaata cggaattaag tcaatcaaat attgaagaaa gatataaaat tcaatcatat    3240
agcgaatatt taaagattt ttggggaaat cctttaatgt agaataaaga atattatatg    3300
tttaatgcgg ggaataaaaa ttcatatatt aaactaaaga aagattcacc tgtaggtgaa    3360
attttaacac gtagcaaata taatcaaaat tctaaatata taaattatag agatttatat    3420
attggagaaa aatttattat aagaagaaag tcaaattctc aatctataaa tgatgatata    3480
gttagaaaag aagattatat atatctagat tttttaatt taaatcaaga gtggagagta    3540 tataccctata aatatttaa gaagaggaa gaaaaattgt ttttagctcc tataagtgat    3600
tctgatgagt tttagaatac tatacaaata aagagaatatg atgaacagcc aacatataat    3660
tgtcagttgc tttttaaaaa agatgaagaa agtactgatg agataggatt gattggtatt    3720 catcgttct aggaatctgg aattgtattt gaagagtata aagattattt ttgtataagt    3780
aaatggtagt taaagaggt aaaaaggaaa ccatataatt taaaattggg atgtaattgg    3840
cagtttattc ctaaagatga agggtggact gaataa                              3876

<210> SEQ ID NO 4
<211> LENGTH: 3876
<212> TYPE: DNA
<213> ORGANISM: botulinum toxin

<400> SEQUENCE: 4
atgccaataa caattaacaa ctttaattat tcagatcctg ttgataataa aaatattta    60 tatttagata ctcatttaaa tacactagct aatgagcctg aaaaagcctt tcgcattaca    120
```

```
ggaaatatat gggtaatacc tgatagattt tcaagaaatt ctaatccaaa tttaaataaa    180
cctcctcgag ttacaagccc taaaagtggt tattatgatc ctaattattt gagtactgat    240
tctgacaaag atacattttt aaaagaaatt ataaagttat ttaaaagaat taattctaga    300
gaaataggag aagaattaat atatagactt tcgacagata tacccttttcc tgggaataac    360 aatactccaa ttaatacttt tgattttgat gtagatttta acagtgttga tgttaaaact    420
agacaaggta acaactgggt taaaactggt agcataaatc ctagtgttat aataactgga    480
cctagagaaa acattataga tccagaaact tctacgttta aattaactaa caatacttttt   540 gcggcacaag aaggatttgg tgctttatca ataatttcaa tatcacctag atttatgcta    600
acatatagta atgcaactaa tgatgtagga gagggtagat tttctaagtc tgaattttgc    660
atggatccaa tactaatttt aatgcatgaa cttaatcatg caatgcataa tttatatgga    720
atagctatac caaatgatca aacaatttca tctgtaacta gtaatatttt ttattctcaa    780
tataatgtga aattagagta tgcagaaata tatgcatttg gaggtccaac tatagacctt    840
attcctaaaa gtgcaaggaa atattttgag gaaaaggcat tggattatta tagatctata    900
gctaaaagac ttaatagtat aactactgca aatccttcaa gctttaataa atatataggg    960
gaatataaac agaaacttat tagaaagtat agattcgtag tagaatcttc aggtgaagtt   1020
acagtaaatc gtaataagtt tgttgagtta tataatgaac ttacacaaat atttacagaa   1080
tttaactagg ctaaaatata taatgtacaa aataggaaaa tatatctttc aaatgtatat   1140
actccggtta cggcgaatat attagacgat aatgtttatg atatacaaaa tggatttaat   1200
atacctaaaa gtaatttaaa tgtactattt atgggtcaaa atttatctcg aaatccagca   1260
ttaagaaaag tcaatcctga aaatatgctt tatttattta caaaattttg tcataaagca   1320
atagatggta gatcattata taataaaaca ttagattgta gagagctttt agttaaaaat   1380
actgacttac cctttatagg tgatattagt gatgttaaaa ctgatatatt tttaagaaaa   1440
gatattaatg aagaaactga agttatatac tatccggaca atgtttcagt agatcaagtt   1500
attctcagta agaataccctc agaacatgga caactagatt tattataccc tagtattgac   1560
agtgagagtg aaatattacc aggggagaat caagtctttt atgataatag aactcaaaat   1620
gttgattatt tgaattctta ttattaccta gaatctcaaa aactaagtga taatgttgaa   1680
gattttactt ttacgagatc aattgaggag gctttggata tagtgcaaa agtatatact   1740 tactttccta cactagctaa taaagtaaat gcgggtgttc aaggtggttt attttttaatg  1800 tgggcaaatg atgtagttga agattttact acaaatattc taagaaaaga tacattagat   1860
aaaatatcag atgtatcagc tattattccc tatataggac ccgcattaaa tataagtaat   1920
tctgtaagaa gaggaaattt tactgaagca tttgcagtta ctggtgtaac tatttttatta  1980 gaagcatttc ctgaatttac aatacctgca cttggtgcat ttgtgattta tagtaaggtt   2040
caagaaagaa acgagattat taaaactata gataattgtt tagaacaaag gattaagaga   2100
tggaaagatt catatgaatg gatgatggga acgtggttat ccaggattat tactcaatttt   2160 aataatataa gttatcaaat gtatgattct ttaaattatc aggcaggtgc aatcaaagct   2220
aaaatagatt tagaatataa aaaatattca ggaagtgata agaaaatat aaaaagtcaa   2280 gttgaaaatt taaaaatag tttagatgta aaatttcgg aagcaatgaa taatataaat   2340
aaatttatac gagaatgttc cgtaacatat ttatttaaaa atatgttacc taaagtaatt   2400
gatgaattaa atgagtttga tcgaaatact aaagcaaat taattaatct tatagatagt   2460
cataatatta ttctagttgg tgaagtagat aaattaaaag caaaagtaaa aatagctttt   2520
```

| | |
|---|---|
| caaaatacaa taccctttaa tattttttca tatactaata attctttatt aaaagatata | 2580 |
| attaatgaat atttcaataa tattaatgat tcaaaaattt tgagcctaca aaacagaaaa | 2640 |
| aatactttag tggatacatc aggatataat gcagaagtga gtgaagaagg cgatgttcag | 2700 |
| cttaatccaa tatttccatt tgactttaaa ttaggtagtt caggggagga tagaggtaaa | 2760 |
| gttatagtaa cccagaatga aaatattgta tataattcta tgtatgaaag ttttagcatt | 2820 |
| agttttggga ttagaataaa taaatgggta agtaatttac ctggatatac tataattgat | 2880 |
| agtgttaaaa ataactcagg ttggagtata ggtattatta gtaattttt agtatttact | 2940 |
| ttaaaacaaa atgaagatag tgaacaaagt ataaattta gttatgatat atcaaataat | 3000 |
| gctcctggat agaataaatg gttttttgta actgttacta acaatatgat gggaaatatg | 3060 |
| aagatttata taaatggaaa attaatagat actataaaag ttaaagaact aactggaatt | 3120 |
| aattttagca aaactataac atttgaaata aataaaattc cagataccgg tttgattact | 3180 |
| tcagattctg ataacatcaa tatgtggata agagattttt atatatttgc taaagaatta | 3240 |
| gatggtaaag atattaatat attatttaat agcttgcaat atactaatgt tgtaaaagat | 3300 |
| tattggggaa atgatttaag atataataaa gaatatttata tggttaatat agattattta | 3360 |
| aatagatata tgtatgcgaa ctcacgacaa attgtttta atacacgtag aaataataat | 3420 |
| gacttcaatg aaggatataa aattataata aaagaatca gaggaaatac aaatgatact | 3480 |
| agagtacgag gaggagatat tttatatttt gatatgacaa ttaataacaa agcatataat | 3540 |
| ttgtttatga agaatgaaac tatgtatgca gataatcata gtactgaaga tatatatgct | 3600 |
| ataggtttaa gagaacaaac aaaggatata aatgataata ttatatttca aatacaacca | 3660 |
| atgaataata cttattatta ggcatctcaa atatttaaat caaattttaa tggagaaaat | 3720 |
| atttctggaa tatgttcaat aggtacttat cgttttagac ttggaggtga ttggtataga | 3780 |
| cacaattatt tggtgcctac tgtgaagcaa ggaaattatg cttcattatt agaatcaaca | 3840 |
| tcaactcatt ggggttttgt acctgtaagt gaataa | 3876 |

<210> SEQ ID NO 5
<211> LENGTH: 3831
<212> TYPE: DNA
<213> ORGANISM: botulinum toxin

<400> SEQUENCE: 5

| | |
|---|---|
| atgacatggc cagtaaaaga ttttaattat agtgatcctg ttaatgacaa tgatatatta | 60 |
| tatttaagaa taccacaaaa taagttaatt actacacctg taaaagcttt tatgattact | 120 |
| caaaatattt gggtaatacc agaaagattt tcatcagata ctaatccaag tttaagtaaa | 180 |
| ccgcccagac tacttcaaa gtatcaaagt tattatgatc ctagttattt atctactgat | 240 |
| gaacaaaaag atacatttt aaaagggatt ataaaattat ttaaagaat taatgaaaga | 300 |
| gatataggaa aaaattaat aaattattta gtagttggtt cacctttat gggagattca | 360 |
| agtacgcctg aagatacatt tgatttaca cgtcatacta ctaatattgc agttgaaaag | 420 |
| tttgaaaatg gtagttggaa agtaacaaat attataacac aagtgtatt gatatttgga | 480 |
| ccacttccta atatattaga ctatacagca tcccttacat tgcaaggaca acaatcaaat | 540 |
| ccatcatttg aagggtttgg aacattatct atactaaaag tagcacctga atttttgtta | 600 |
| acatttagtg atgtaacatc taatcaaagt tcagctgtat taggcaaatc tatattttgt | 660 |
| atggatccag taatagcttt aatgcatgag ttaacacatt ctttgcatca attatatgga | 720 |
| ataaatatac catctgataa aaggattcgt ccacaagtta gcgagggatt tttctctcaa | 780 |

```
gatggaccca acgtacaatt tgaggaatta tatacatttg gaggattaga tgttgaaata      840
atacctcaaa ttgaaagatc acaattaaga gaaaaagcat taggtcacta taaagatata      900
gcgaaaagac ttaataatat taataaaact attccttcta gttggattag taatatagat      960
aaatataaaa aaatattttc tgaaaagtat aattttgata agataatac aggaaatttt      1020
gttgtaaata ttgataaatt caatagctta tattcagact tgactaatgt tatgtcagaa     1080
gttgtttatt cttcgcaata taatgttaaa aacaggactc attattttc aaggcattat      1140
ctacctgtat ttgcaaatat attagatgat aatatttata ctataagaga tggttttaat     1200
ttaacaaata aaggttttaa tatagaaaat tcgggtcaga atatagaaag gaatcctgca     1260
ctacaaaagc ttagttcaga aagtgtagta gatttattta caaaagtatg tttaagatta     1320
acaaaaaata gtagagatga ttcaacatgt attaaagtta aaaataatag attaccttat     1380
gtagctgata aagatagcat ttcacaagaa atatttgaaa ataaaattat tacagatgag     1440
actaatgtac aaaattattc agataatttt tcattagatg aatctatttt agatgggcaa     1500
gttcctatta atcctgaaat agtagatcca ctattaccca atgttaatat ggaacctta     1560
aatcttccag gtgaagaaat agtattttat gatgatatta ctaaatatgt tgattattta     1620
aattcttatt attatttgga atctcaaaaa ttaagtaata atgttgaaaa tattactctt     1680
acaacttcag ttgaagaagc attaggttat agcaataaga tatagacatt tttacctagc     1740
ttagctgaaa aagtgaataa aggtgttcaa gcaggtttat tcttaaattg ggcgaatgaa     1800
gtagttgagg atttactac aaatattatg aagaaagata cattggataa aatatcagat     1860
gtatcagtaa taattccata tataggacct gccttaaata taggaaattc agcattaagg     1920
ggaaatttta agcaagcatt tgcaacagct ggtgtagctt ttttattaga gggatttcca     1980
gagtttacta tacctgcact cggtgtattt accttttata gttctattca agaaagagag     2040
aaaattatta aaactataga aaattgtttg gaacaaagag ttaagagatg gaaagattca     2100
tatcaatgga tggtatcaaa ttggttgtca agaattacta ctcaatttaa tcatataaat     2160
tatcaaatgt atgattcttt aagttatcag gcagatgcaa tcaaagctaa aatagattta     2220
gaatataaaa aatagtcagg aagtgataaa gaaaatataa aaagtcaagt tgaaaattta     2280
aaaaatagtt tagatgtaaa aatttcggaa gcaatgaata atataaataa atttatacga     2340
gaatgttctg taacatagtt attaaaaat atgctcccta aagtaattga cgaattaaat     2400
aagtttgatt taagaactaa aacagaatta attaatctta tagatagtca taatattatt     2460
ctagttggtg aagtagatag attaaaagca aaagtaaatg agagttttga aaatacaatg     2520
ccttttaata tttttcata tactaataat tctttattaa aagatataat taatgaatat     2580
ttcaatagta ttaatgattc aaaaattttg agcttacaaa acaaaaaaaa tgctttagtg     2640
gatacatcag gatataatgc agaagtgagg gtaggagata atgttcaact taatacgata     2700
tatacaaatg actttaaatt aagtagttca ggagataaaa ttatagtaaa tttaaataat     2760
aatattttat atagcgctat ttatgagaac tctagtgtta gttttggat taagatatct     2820
aaagatttaa ctaattctca taatgaatat acaataatta acagtataga acaaaattct     2880
gggtggaaat tatgtattag gaatggcaat atagaatgga ttttacaaga tgttaataga     2940
aagtataaaa gtttaatttt tgattatagt gaatcattaa gtcatacagg atatacaaat     3000
aaatggtttt ttgttactat aactaataat ataatggggt atatgaaact ttatataaat     3060
ggagaattaa agcagagtca aaaaattgaa gatttagatg aggttaagtt agataaaacc     3120
atagtatttg gaatagatga gaatatagat gagaatcaga tgcttggat tagagatttt     3180
```

-continued

| aatatttttt ctaaagaatt aagtaatgaa gatattaata ttgtatatga gggacaaata | 3240 |
| ttaagaaatg ttattaaaga ttattgggga aatcctttga agtttgatac agaatattat | 3300 |
| attattaatg ataattatat agataggtat attgcacctg aaagtaatgt acttgtactt | 3360 |
| gttcggtatc cagatagatc taaattatat actggaaatc ctattactat taaatcagta | 3420 |
| tctgataaga atccttatag tagaatttta aatggagata atataattct tcatatgtta | 3480 |
| tataatagta ggaaatatat gataataaga gatactgata caatatatgc aacacaagga | 3540 |
| ggagagtgtt cacaaaattg tgtatatgca ttaaaattac agagtaattt aggtaattat | 3600 |
| ggtataggta tatttagtat aaaaaatatt gtatctaaaa ataaatattg tagtcaaatt | 3660 |
| ttctctagtt ttagggaaaa tacaatgctt ctagcagata tatataaacc ttggagattt | 3720 |
| tcttttaaaa atgcatagac gccagttgca gtaactaatt atgaaacaaa actattatca | 3780 |
| acttcatctt tttggaaatt tatttctagg gatccaggat gggtagagta a | 3831 |

<210> SEQ ID NO 6
<211> LENGTH: 3753
<212> TYPE: DNA
<213> ORGANISM: botulinum toxin

<400> SEQUENCE: 6

| atgccaacaa ttaatagttt taattataat gatcctgtta ataatagaac aattttatat | 60 |
| attaaaccag gcggttgtca acaatttat aaatcattta atattatgaa aaatatttgg | 120 |
| ataattccag agagaaatgt aattggtaca attccccaag atttttcttcc gcctacttca | 180 |
| ttgaaaaatg gagatagtag ttattatgac cctaattatt tacaaagtga tcaagaaaag | 240 |
| gataaattt taaaaatagt cacaaaaata tttaatagaa taaatgataa tctttcagga | 300 |
| aggatttat tagaagaact gtcaaaagct aatccatatt taggaaatga taatactcca | 360 |
| gatggtgact tcattattaa tgatgcatca gcagttccaa ttcaattctc aaatggtagc | 420 |
| caaagcatac tattacctaa tgttattata atgggagcag agcctgattt atttgaaact | 480 |
| aacagttcca atatttctct aagaaataat tatatgccaa gcaatacgg ttttggatca | 540 |
| atagctatag taacattctc acctgaatat tcttttagat ttaaagataa tagtatgaat | 600 |
| gaatttattc aagatcctgc tcttacatta atgcatgaat aatacattc attacatgga | 660 |
| ctatatgggg ctaaagggat tactacaaag tatactataa cacaaaaaca aaatccccta | 720 |
| ataacaaata taagaggtac aaatattgaa gaattcttaa cttttggagg tactgattta | 780 |
| aacattatta ctagtgctca gtccaatgat atctatacta atcttctagc tgattataaa | 840 |
| aaaatagcgt ctaaacttag caaagtacaa gtatctaatc cactacttaa tccttataaa | 900 |
| gatgttttg aagcaaagta tggattagat aaagatgcta gcggaattta ttcggtaaat | 960 |
| ataaacaaat ttaatgatat ttttaaaaaa ttatacagct ttacggaatt tgatttagca | 1020 |
| actaaatttc aagttaaatg taggcaaact tatattggac agtataaata cttcaaactt | 1080 |
| tcaaacttgt taaatgattc tatttataat atatcagaag gctataatat aaataattta | 1140 |
| aaggtaaatt ttagaggaca gaatgcaaat ttaaatccta gaattattac accaattaca | 1200 |
| ggtagaggac tagtaaaaaa aatcattaga ttttgtaaaa atattgtttc tgtaaaaggc | 1260 |
| ataaggaaat caatatgtat cgaaataaat aatggtgagt tatttttttgt ggcttccgag | 1320 |
| aatagttata atgatgataa tataaatact cctaaagaaa ttgacgatac agtaacttca | 1380 |
| aataataatt atgaaaatga tttagatcag gttattttaa attttaatag tgaatcagca | 1440 |
| cctggacttt cagatgaaaa attaaattta actatccaaa atgatgctta tataccaaaa | 1500 |

-continued

```
tatgattcta atggaacaag tgatatagaa caacatgatg ttaatgaact taatgtattt    1560
ttctatttag atgcacagaa agtgcccgaa ggtgaaaata atgtcaatct cacctcttca    1620
attgatacag cattattaga acaacctaaa atatatacat ttttttcatc agaatttatt    1680
aataatgtca ataaacctgt gcaagcagca ttatttgtaa gctggataca acaagtatta    1740
gtagatttta ctactgaagc taaccaaaaa agtactgttg ataaaattgc agatatttct    1800
atagttgttc catatatagg tcttgcttta aatataggaa atgaagcaca aaaggaaat    1860 tttaaagatg cacttgaatt attaggagca ggtatttat tagaatttga acccgagctt    1920
ttaattccta caattttagt attcacgata aaatcttttt taggttcatc tgataataaa    1980
aataaagtta ttaaagcaat aaataatgca ttgaaagaaa gagatgaaaa atggaaagaa    2040
gtatatagtt ttatagtatc gaattggatg actaaaatta atacacaatt taataaaaga    2100
aaagaacaaa tgtatcaagc tttacaaaat caagtaaatg cacttaaagc aataatagaa    2160
tctaagtata atagttatac tttagaagaa aaaaatgagc ttacaaataa atatgatatt    2220
gagcaaatag aaaatgaact taatcaaaag gtttctatag caatgaataa tatagacagg    2280
ttcttaactg aaagttctat atcttattta atgaaattaa taaatgaagt aaaaattaat    2340
aaattaagag aatatgatga aaatgttaaa acgtatttat tagattatat tataaaacat    2400
ggatcaatct tgggagagag tcagcaagaa ctaaattcta tggtaattga tacccctaaat   2460 aatagtattc ctttttaagct ttcttcttat acagatgata aaattttaat ttcatatttt    2520
aataagttct ttaagagaat taaaagtagt tctgttttaa atatgagata taaaaatgat    2580
aaataggtag atacttcagg atatgattca aatataaata ttaatggaga tgtatataaa    2640
tatccaacta ataaaaatca atttggaata tataatgata aacttagtga agttaatata    2700
tctcaaaatg attacattat atatgataat aaatataaaa attttagtat tagttttgg     2760 gtaagaattc ctaactatga taataagata gtaaatgtta ataatgaata cactataata    2820
aattgtatga gggataataa ttcaggatgg aaagtatctc ttaatcataa tgaaataatt    2880
tggacattgc aagataattc aggaattaat caaaaattag catttaacta tggtaacgca    2940 aatggtatt ctgattatat aaataagtgg attttttgtaa ctataactaa tgatagatta    3000
ggagattcta aacttttatat taatggaaat ttaatagata aaaaatcaat tttaaattta    3060
ggtaatattc atgttagtga caatatatta tttttaaatag ttaattgtag ttatacaaga    3120
tatattggta ttagatattt taatatttt gataaagaat tagatgaaac agaaattcaa    3180
actttatata caatgaacc taatgcaaat attttaaagg attttggggg aaattattg     3240 ctttatgaca agaatagta tttattaaat gtgttaaaac caaataactt tattaatagg    3300
agaacagatt ctactttaag cattaataat ataagaagca ctattctttt agctaataga    3360
ttatatagtg gaataaaagt taaaatacaa agagttaata atagtagtac taacgataat    3420
cttgttagaa agaatgatca ggtatatatt aattttgtag ccagcaaaac tcacttactt    3480
ccattatatg ctgatacagc taccacaaat aaagagaaaa caataaaaat atcatcatct    3540
ggcaatagat ttaatcaagt agtagttatg aattcagtag gatgtacaat gaattttaaa    3600
aataataatg gaaataatat tgggttgtta ggtttcaagg cagatactgt agttgctagt    3660
acttggtatt atacacatat gagagataat acaaacagca atggattttt ttggaacttt    3720
atttctgaag aacatggatg gcaagaaaaa taa                                 3753
```

<210> SEQ ID NO 7
<211> LENGTH: 3759
<212> TYPE: DNA

<213> ORGANISM: botulinum toxin

<400> SEQUENCE: 7

| | | | | | |
|---|---|---|---|---|---|
| atgccaaaaa | ttaatagttt | taattataat | gatcctgtta | atgatagaac | aattttatat | 60 |
| attaaaccag | gcggttgtca | agaatttat | aaatcattta | atattatgaa | aaatatttgg | 120 |
| ataattccag | agagaaatgt | aattggtaca | acccccccaag | attttcatcc | gcctacttca | 180 |
| ttaaaaaatg | gagatagtag | ttattatgac | cctaattatt | tacaaagtga | tgaagaaaag | 240 |
| gatagatttt | taaaaatagt | cacaaaaata | tttaatagaa | taaataataa | tctttcagga | 300 |
| gggatttat | tagaagaact | gtcaaaagct | aatccatatt | tagggaatga | taatactcca | 360 |
| gataatcaat | tccatattgg | tgatgcatca | gcagttgaga | ttaaattctc | aaatggtagc | 420 |
| caagacatac | tattacctaa | tgttattata | atgggagcag | agcctgattt | atttgaaact | 480 |
| aacagttcca | atatttctct | aagaaataat | tatatgccaa | gcaatcacgg | ttttggatca | 540 |
| atagctatag | taacattctc | acctgaatat | tcttttagat | ttaatgataa | tagtatgaat | 600 |
| gaatttattc | aagatcctgc | tcttacatta | atgcatgaat | aatacattc | attacatgga | 660 |
| ctatatgggg | ctaaagggat | tactacaaag | tatactataa | cacaaaaaca | aaatccccta | 720 |
| ataacaaata | taagaggtac | aaatattgaa | gaattcttaa | cttttggagg | tactgattta | 780 |
| aacattatta | ctagtgctca | gtccaatgat | atctatacta | atcttctagc | tgattataaa | 840 |
| aaaatagcgt | ctaaacttag | caaagtacaa | gtatctaatc | cactacttaa | tccttataaa | 900 |
| gatgtttttg | aagcaaagta | tggattagat | aaagatgcta | gcggaattta | ttcggtaaat | 960 |
| ataaacaaat | ttaatgatat | ttttaaaaaa | ttatagagct | ttacggaatt | tgatttagca | 1020 |
| actaaatttc | aagttaaatg | taggcaaact | tatattggac | agtataaata | cttcaaactt | 1080 |
| tcaaacttgt | taaatgattc | tatttataat | atatcagaag | gctataatat | aaataattta | 1140 |
| aaggtaaatt | ttagaggaca | gaatgcaaat | ttaaatccta | gaattattac | accaattaca | 1200 |
| ggtagaggac | tagtaaaaaa | aatcattaga | ttttgtaaaa | atattgtttc | tgtaaaaggc | 1260 |
| ataaggaaat | caatatgtat | cgaaataaat | aatggtgagt | tatttttgt | ggcttccgag | 1320 |
| aatagttata | atgatgataa | tataaatact | cctaaagaaa | ttgacgatac | agtaacttca | 1380 |
| aataataatt | atgaaaatga | tttagatcag | gttattttaa | attttaatag | tgaatcagca | 1440 |
| cctggacttt | cagatgaaaa | attaaattta | actatccaaa | atgatgctta | taccaaaa | 1500 |
| tatgattcta | atggaacaag | tgatatagaa | caacatgatg | ttaatgaact | taatgtattt | 1560 |
| ttctatttag | atgcacagaa | agtgcccgaa | ggtgaaaata | atgtcaatct | cacctcttca | 1620 |
| attgatacag | cattattaga | acaacctaaa | atatatacat | ttttttcatc | agaatttatt | 1680 |
| aataatgtca | ataaacctgt | gcaagcagca | ttatttgtaa | gctggataca | acaagtgtta | 1740 |
| gtagatttta | ctactgaagc | taaccaaaaa | agtactgttg | ataaaattgc | agatatttct | 1800 |
| atagttgttc | catatatagg | tcttgcttta | aatataggaa | atgaagcaca | aaaaggaaat | 1860 |
| tttaaagatg | cacttgaatt | attaggagca | ggtattttat | tagaatttga | acccgagctt | 1920 |
| ttaattccta | caatttagt | attcacgata | aaatctttt | taggttcatc | tgataataaa | 1980 |
| aataaagtta | ttaaagcaat | aaataatgca | ttgaaagaaa | gagatgaaaa | atggaaagaa | 2040 |
| gtatatagtt | ttatagtatc | gaattggatg | actaaaatta | atacacaatt | taataaaaga | 2100 |
| aaagaacaaa | tgtatcaagc | tttacaaaat | caagtaaatg | caattaaaac | aataatagaa | 2160 |
| tctaagtata | atagttatac | tttagaggaa | aaaaatgagc | ttacaaataa | atatgatatt | 2220 |
| aagcaaatag | aaaatgaact | taatcaaaag | gtttctatag | caatgaataa | tatagacagg | 2280 |

-continued

```
ttcttaactg aaagttctat atcctatttta atgaaattaa taaatgaagt aaaaattaat    2340
aaattaagag aatatgatga gaatgtcaaa acgtatttat tgaattatat tatacaacat    2400
ggatcaatct tgggagagag tcagcaagaa ctaaattcta tggtaactga taccctaaat    2460
aatagtattc cttttaagct ttcttcttat acagatgata aaattttaat ttcatatttt    2520
aataaattct ttaagagaat taaaagtagt tcagttttaa atatgagata taaaaatgat    2580
aaatacgtag atacttcagg atatgattca aatataaata ttaatggaga tgtatataaa    2640
tatccaacta ataaaaatca atttggaata tataatgata aacttagtga agttaatata    2700
tctcaaaatg attagattat atatgataat aaatataaaa attttagtat tagttttttgg    2760
gtaagaattc ctaactatga taataagata gtaaatgtta ataatgaata gactataata    2820
aattgtatga gagataataa ttcaggatgg aaagtatctc ttaatcataa tgaataatt    2880
tggacattgc aagataatgc aggaattaat caaaaattag catttaacta tggtaacgca    2940
aatggtatttt ctgattatat aaataagtgg attttttgtaa ctataactaa tgatagatta    3000
ggagattcta aactttatat taatggaaat ttaatagatc aaaaatcaat tttaaattta    3060
ggtaatattc atgttagtga caatatatta tttaaaatag ttaattgtag ttatacaaga    3120
tatattggta ttagatatttt taatattttt gataaagaat tagatgaaac agaaattcaa    3180
actttatata gcaatgaacc taatacaaat attttgaagg attttttgggg aaattatttg    3240
ctttatgaca aagaatacta tttattaaat gtgttaaaac caaataactt tattgatagg    3300
agaaaagatt ctactttaag cattaataat ataagaagca ctattctttt agctaataga    3360
ttatatagtg aataaaaagt taaaatacaa agagttaata atagtagtac taacgataat    3420
cttgttagaa agaatgatca ggtatatatt aatttttgtag ccagcaaaac tcacttattt    3480
ccattatatg ctgatacagc taccacaaat aaagagaaaa caataaaaat atcatcatct    3540
ggcaatagat ttaatcaagt agtagttatg aattcagtag gaaataattg tacaatgaat    3600
tttaaaaata taatggaaa taatattggg ttgttaggtt tcaaggcaga tactgtagtt    3660
gctagtactt ggtattatac acatatgaga gatcatacaa acagcaatgg atgttttttgg    3720
aactttattt ctgaagaaca tggatggcaa gaaaaataa                            3759
```

<210> SEQ ID NO 8
<211> LENGTH: 3825
<212> TYPE: DNA
<213> ORGANISM: botulinum toxin

<400> SEQUENCE: 8

```
atgccagttg caataaatag ttttaattat aatgaccctg ttaatgatga tacaattttta     60
tagatgcaga taccatatga agaaaaaagt aaaaaatatt ataaagcttt tgagattatg    120
cgtaatgttt ggataattcc tgagagaaat acaataggaa cgaatcctag tgattttgat    180
ccaccggctt cattaaagaa cggaagcagt gcttattatg atcctaatta tttaaccact    240
gatgctgaaa agatagata tttaaaaaca acgataaaat tatttaagag aattaatagt    300
aatcctgcag ggaaagtttt gttacaagaa atatcatatg ctaaaccata tttaggaaat    360
gaccacacgc caattgatga attctctcca gttactagaa ctacaagtgt taatataaaa    420
ttatcaacta atgttgaaag ttcaatgtta ttgaatcttc ttgtattggg agcaggacct    480
gatatatttg aaagttgttg ttaccccgtt agaaaactaa tagatccaga tgtagtttat    540
gatccaagta ttatggttt tggatcaatt aatatcgtga catttttcacc tgagtatgaa    600
tatactttta atgatattag tggagggcat aatagtagta cagaatcatt tattgcagat    660
```

```
cctgcaattt cactagctca tgaattgata catgcactgc atggattata cggggctagg    720
ggagttactt atgaagagac tatagaagta aagcaagcac ctcttatgat agccgaaaaa    780
cccataaggc tagaagaatt tttaaccttt ggaggtcagg atttaaatat tattactagt    840
gctatgaagg aaaaaatata taacaatctt ttagctaact atgaaaaaat agctactaga    900
cttagtgaag ttaatagtgc tcctcctgaa tatgatatta atgaatataa agattatttt    960
caatggaagt atgggctaga taaaaatgct gatggaagtt atactgtaaa tgaaaataaa   1020
tttaatgaaa tttataaaaa attatatagt tttacagaga gtgacttagc aaataaattt   1080
aaagtaaaat gtagaaatac ttattttatt aaatatgaat ttttaaaagt tccaaatttg   1140
ttagatgatg atatttatac tgtatcagag gggtttaata taggtaattt agcagtaaac   1200
aatcgcggac aaagtataaa gttaaatcct aaaattattg attccattcc agataaaggt   1260
ctagtagaaa agatcgttaa attttgtaag agcgttattc ctagaaaagg tacaaaggcg   1320
ccaccgcgac tatgcattag agtaaataat agtgagttat tttttgtagc ttcagaaagt   1380
agctataatg aaaatgatat taatacacct aaagaaattg acgatacaac aaatctaaat   1440
aataattata gaaataattt agatgaagtt attttagatt ataatagtca gacaatacct   1500
caaatatcaa atcgaacatt aaatacactt gtacaagaca atagttatgt gccaagatat   1560
gattctaatg aacaagtga aatagaggaa tatgatgttg ttgactttaa tgtatttttc   1620
tatttacatg cacaaaaagt gccagaaggt gaaaccaata taagtttaac ttcttcaatt   1680
gatacagcat tattgaaga atccaaagat atatttttt cttcagagtt tatcgatact   1740
atcaataaac ctgtaaatgc agcactattt atagattgga taagcaaagt aataagagat   1800
tttaccactg aagctacaca aaaaagtact gttgataaga ttgcagacat atctttaatt   1860
gtaccctatg taggtcttgc tttgaatata attattgagg cagaaaaagg aaattttgag   1920
gaggcatttg aattattagg agtgggtatt ttattagaat ttgtgccaga acttacaatt   1980
cctgtaattt tagtgtttac gataaaatcc tatatagatt catatgagaa taaaaataaa   2040
gcaattaaag caataaataa ttcattaatc gaaagagaag caaagtggaa agaaatatat   2100
agttggatag tatcaaattg gcttactaga attaatactc aatttaataa aagaaaagag   2160
caaatgtatc aggctttaca aaatcaagta gatgcaataa aaacagcaat agaatataaa   2220
tataataatt atacttcaga tgagaaaaat agacttgaat ctgaatataa tatcaataat   2280
atagaagaag aattgaataa aaaagtttct ttagcaatga aaaatataga aagatttatg   2340
acagaaagtt ctatatctta tttaatgaaa ttaataaatg aagccaaagt tggtaaatta   2400
aaaaaatatg ataaccatgt taagagcgat ttattaaact atattctcga ccatagatca   2460
atcttaggag agcagacaaa tgaattaagt gatttggtga ctagtacttt gaatagtagt   2520
attccatttg aactttcttc atatactaat gataaaattc taattatata ttttaataga   2580
ttatataaaa aaattaaaga tagttctatt ttagatatgc gatatgaaaa taataaattt   2640
atagatatct ctggatatgg ttcaaatata agcattaatg gaaacgtata tatttattca   2700
acaaatagaa atcaatttgg aatatataat agtaggctta gtgaagttaa tatagctcaa   2760
aataatgata ttatatagaa tagtagatat caaaatttta gtattagttt ctgggtaagg   2820
attcctaaac actagaaacc tatgaatcat aatcgggaat agactataat aaattgtatg   2880
gggaataata attcgggatg gaaaatatca cttagaactg ttagagattg tgaaataatt   2940
tggactttac aagatacttc tggaaataag gaaaatttaa tttttaggta tgaagaactt   3000
aataggatat ctaattatat aaataaatgg attttttgtaa ctattactaa taatagatta   3060
```

```
ggcaattcta gaatttagat caatggaaat ttaatagttg aaaaatcaat ttcgaattta      3120
ggtgatattc atgttagtga taatatatta tttaaaattg ttggttgtga tgatgaaacg      3180
tatgttggta taagatattt taaagttttt aatacggaat tagataaaac agaaattgag      3240
actttatata gtaatgagcc agatccaagt atcttaaaaa actattgggg aaattatttg      3300
ctatataata aaaaatatta tttattcaat ttactaagaa agataagta tattactctg       3360 aattcaggca ttttaaatat taatcaacaa agaggtgtta ctgaaggctc tgttttttg       3420 aactataaat tatatgaagg agtagaagtc attataagaa aaaatggtcc tatagatata      3480
tctaatacag ataattttgt tagaaaaaac gatctagcat acattaatgt agtagatcgt      3540
ggtgtagaat atcggttata tgctgataca aaatcagaga agagaaaaat aataagaaca      3600
tctaatctaa acgatagctt aggtcaaatt atagttatgg attcaatagg aaataattgc      3660
acaatgaatt ttcaaaacaa taatgggagc aatataggat tactaggtttt tcattcaaat      3720 aatttggttg ctagtagttg gtattataac aatatacgaa gaaatactag cagtaatgga      3780
tgcttttgga gttctatttc taaagagaat ggatggaaag aatga                     3825

<210> SEQ ID NO 9
<211> LENGTH: 3894
<212> TYPE: DNA
<213> ORGANISM: Artificial Sequence
<220> FEATURE:
<223> OTHER INFORMATION: Description of Artificial Sequence: synthetic
      primers used to introduce Stu I and EcoR I
      restriction sites into the 5' and 3' ends of the
      BoNT/A-L chain gene fragment

<400> SEQUENCE: 9
atgccagtta atataaaaaa ctttaattat aatgaccota ttaataatga tgacattatt        60
atgatggaac cattcaatga cccagggcca ggaacatatt ataaagcttt taggattata       120 gatcgtatttt ggatagtacc agaaaggttt acttatggat ttcaacctga ccaatttaat      180
gccagtacag gagttttag taaagatgtc tacgaatatt aggatccaac ttatttaaaa       240
accgatgctg aaaagataa attttttaaaa acaatgatta aattatttaa tagaattaat      300
tcaaaaccat caggacagag attactggat atgatagtag atgctatacc ttatcttgga     360
aatgcatcta caccgcccga caatttgca gcaaatgttg caaatgtatc tattaataaa      420
aaaattatcc aacctggagc tgaagatcaa ataaaaggtt aatgacaaa tttaataata     480 tttggaccag accagttct aagtgataat tttactgata gtatgattat gaatggccat      540
tccccaatat cagaaggatt tggtgcaaga tgatgataaa gattttgtcc tagttgttta     600 aatgtatta ataatgttca ggaaaataaa gatacatcta tatttagtag acgcgcgtat      660
tttgcagatc cagctctaac gttaatgcat gaacttatac atgtgttaca tggattatat     720
ggaattaaga taagtaattt accaattact ccaaatacaa agaatttttt catgcaacat     780
agcgatcctg tacaagcaga agaactatat acattcggag gacatgatcc tagtgttata     840
agtccttcta cggatatgaa tatttataat aaagcgttac aaaattttca agatatagct      900
aataggctta tatattgttc aagtgcccaa gggagtggaa ttgatatttc cttatataaa     960
caaatatata aaaataaata tgattttgtt gaagatccta atggaaaata tagtgtagat     1020
aaggataagt ttgataaatt ataaggcc ttaatgtttg gctttactga aactaatcta      1080
gctggtgaat atggaataaa aactaggtat tcttattttta gtgaatattt gccaccgata     1140
aaaactgaaa aattgttaga caatacaatt tatactcaaa atgaaggctt taacatagct     1200
agtaaaaatc tcaaaacgga atttaatggt cagaataagg cggtaaataa agaggcttat     1260
```

```
gaagaaatca gcctagaaca tctcgttata tatagaatag caatgtgcaa gcctgtaatg   1320
tacaaaaata ccggtaaatc tgaacagtgt attattgtta ataatgagga tttattttc    1380 atagctaata aagatagttt ttcaaaagat ttagctaaag cagaaactat agcatataat   1440
acacaaaata atactataga aaataatttt tctatagatc agttgatttt agataatgat   1500
ttaagcagtg gcatagactt accaaatgaa aacacagaac catttacaaa ttttgacgac   1560
atagatatcc ctgtgtatat taaacaatct gctttaaaaa aaattttgt ggatggagat    1620 agccttttg aatatttaca tgctcaaaca tttccttcta atatagaaaa tctacaacta    1680
acgaattcat taaatgatgc tttaagaaat aataataaag tctatacttt ttttctaca    1740 aaccttgttg aaaaagctaa tacagttgta ggtgcttcac tttttgtaaa ctgggtaaaa   1800
ggagtaatag atgattttac atctgaatcc acacaaaaaa gtactataga taaagtttca   1860
gatgtatcca taattattcc ctatataga cctgctttga atgtaggaaa tgaaacagct    1920
aaagaaaatt ttaaaaatgc ttttgaaata ggtggagccg ctatcttaat ggagtttatt   1980
ccagaactta ttgtacctat agttggattt tttacattag aatcatatgt aggaaataaa   2040
gggcatatta ttatgacgat atccaatgct ttaaagaaaa gggatcaaaa atggacagat   2100
atgtatggtt tgatagtatc gcagtggctc tcaacggtta atactcaatt ttatacaata   2160
aaagaaagaa tgtagaatgc tttaaataat caatcacaag caatgaaaaa aataatagaa   2220
gatcaatata atagatatag tgaagaagat aaaatgaata ttaacattga ttttaatgat   2280
atagatttta aacttaatca agtatataat ttagcaataa acaatataga tgattttata   2340
aaccaatgtt ctatatcata tctaatgaat agaatgattc cattagctgt aaaaaagtta   2400
aaagactttg atgataatct taagagagat ttattggagt atatagatac aaatgaacta   2460
tatttacttg atgaagtaaa tattctaaaa tcaaaagtaa atagacacct aaaagacagt   2520
ataccatttg atctttcact atataccaag gacacaattt taatacaagt ttttaataat   2580
tatattagta atattagtag taatgctatt ttaagtttaa gttatagagg tgggcgttta   2640
atagattcat ctggatatgg tgcaactatg aatgtaggtt cagatgttat ctttaatgat   2700
ataggaaatg gtcaatttaa attaaataat tctgaaaata gtaatattac ggcacatcaa   2760
agtaaattcg ttgtatatga tagtatgttt gataatttta gcattaactt tgggtaagg    2820 actcctaaat ataataataa tgatatacaa acttatcttc aaaatgagta tacaataatt   2880
agttgtataa aaaatgactc aggatggaaa gtatctatta agggaaatag aataatatgg   2940
acattaatag atgttaatgc aaaatctaaa tcaatatttt tcgaatatag tataaaagat   3000
aatatatcag attatataaa taatggtttt tccataacta ttactaatga tagattaggt   3060
aacgcaaata tttatataaa tggaagtttg aaaaaaagtg aaaaaatttt aaacttagat   3120
agaattaatt ctagtaatga tatagacttc aaattaatta attgtacaga tactactaaa   3180 tttgttttgga ttaaggattt taatattttt ggtagagaat taaatgctac agaagtatct   3240
tcactatatt ggattcaatc atctacaaat actttaaaag attttgggg gaatcctta    3300 agataggata cacaatacta tctgtttaat caaggtatgc aaaatatcta tataaagtat   3360
tttagtaaag cttctatggg ggaaactgca ccacgtacaa actttaataa tgcagcaata   3420
aattatcaaa atttatatct tggtttacga tttattataa aaaaagcatc aaattctcgg   3480
aatataaata atgataatat agtcagagaa ggagattata tatatcttaa tattgataat   3540
atttctgatg aatcttagag agtatatgtt ttggtgaatt ctaagaaaat tcaaactcaa   3600
ttatttttag cacccataaa tgatgatcct acgttctatg atgtactaca aataaaaaaa   3660
```

```
tattatgaaa aaacaacata taattgtcag atactttgcg aaaaagatac taaaacattt    3720
gggctgtttg gaattggtaa atttgttaaa gattatggat atgtttggga tacctatgat    3780
aattattttt gcataagtca gtggtatctc agaagaatat ctgaaaatat aaataaatta    3840
aggttgggat gtaattggca attcattccc gtggatgaag gatggacaga ataa          3894

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:
      oligonucleotide used to introduce Stu I and EcoR I
      into BoNT/A-L chain gene fragments

<400> SEQUENCE: 10
aaaggccttt tgttaataaa caa                                              23

<210> SEQ ID NO 11
<211> LENGTH: 26
<212> TYPE: DNA
<213> ORGANISM: Unknown Organism
<220> FEATURE:
<223> OTHER INFORMATION: Description of Artificial Sequence:
      oligonucleotide used to introduce Stu I and EcoR I
      into BoNT/A-L chain gene fragment

<400> SEQUENCE: 11
ggaattctta cttattgtat ccttta                                           26

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence:
      polypeptide fragment used to raise antibodies

<400> SEQUENCE: 12

Cys Ala Asn Gln Arg Ala Thr Lys Met Leu Gly Ser Gly
 1               5                  10
```